United States Patent [19] [11] 4,279,762
Lewis et al. [45] Jul. 21, 1981

[54] CUTTING OILS CONTAINING 3-ISOTHIAZOLONES AS BIOCIDES

[75] Inventors: Sheldon N. Lewis, Willow Grove; George A. Miller, Glenside; Andrew B. Law, Levittown, all of Pa.

[73] Assignee: Rohm and Haas Company, Philadelphia, Pa.

[21] Appl. No.: 101,594

[22] Filed: Dec. 10, 1979

Related U.S. Application Data

[60] Division of Ser. No. 910,730, May 30, 1978, which is a division of Ser. No. 368,168, Jun. 8, 1973, Pat. No. 4,105,431, which is a continuation-in-part of Ser. No. 836,660, Jun. 25, 1969, Pat. No. 3,761,488, which is a continuation-in-part of Ser. No. 672,437, Oct. 3, 1967, Pat. No. 3,523,121, which is a continuation-in-part of Ser. No. 621,780, Mar. 19, 1967, abandoned.

[51] Int. Cl.$^3$ .............................................. C10M 1/38
[52] U.S. Cl. .................................. 252/47.5; 252/49.5
[58] Field of Search .............................. 252/47.5, 49.5

[56] References Cited

U.S. PATENT DOCUMENTS

| 2,954,343 | 9/1960 | Pitman | 252/49.5 X |
|---|---|---|---|
| 3,377,275 | 4/1968 | Michalski et al. | 252/47.5 X |
| 3,788,989 | 1/1974 | Adams et al. | 252/49.5 X |
| 3,801,575 | 4/1974 | Lewis et al. | 252/47.5 X |
| 3,933,658 | 1/1976 | Beiswanger et al. | 252/49.5 X |
| 4,033,886 | 7/1977 | Felton, Jr. | 252/49.5 X |

FOREIGN PATENT DOCUMENTS 2524543 12/1975 Fed. Rep. of Germany .......... 252/49.5

Primary Examiner—Andrew Metz

[57] ABSTRACT

Disclosed herein are certain novel compounds which are most properly designated as 3-isothiazolones. These compounds and compositions containing them exhibit a broad spectrum of biocidal properties and are particularly effective for the control of microorganisms.

6 Claims, No Drawings

CUTTING OILS CONTAINING 3-ISOTHIAZOLONES AS BIOCIDES

CROSS-REFERENCES TO RELATED APPLICATIONS

This is a division of application Ser. No. 910,730, filed May 30, 1978; which is a division of application Ser. No. 368,168, filed June 8, 1973 and now U.S. Pat. No. 4,105,431; said Ser. No. 368,158 is a continuation-in-part of application Ser. No. 836,660, filed June 25, 1969 and now U.S. Pat. No. 3,761,488; said Ser. No. 836,660 is a continuation-in-part of application Ser. No. 672,437, filed Oct. 3, 1967 and now U.S. Pat. No. 3,523,121; said Serial Number 672,437 is a continuation-in-part of application Ser. No. 621,780, filed on Mar. 19, 1967, and now abandoned.

This invention relates to novel substituted 3-isothiazolones, salts thereof, their preparation, agricultural compositions containing them, and their utilization in the control of living organisms.

These novel 3-isothiazolones (hereinafter referred to at times as "isothiazolones") are represented by the formula

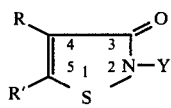

(I)

wherein

Y is an unsubstituted or substituted alkyl, alkenyl, or alkynyl group of 1 to 18 carbon atoms, preferably 4 to 18 carbon atoms, an unsubstituted or substituted cycloalkyl group having a 3 to 12 carbon atom ring, an unsubstituted or substituted aralkyl group of up to 10 carbon atoms, or an unsubstituted or substituted aryl group of up to 10 carbon atoms, R is hydrogen, halogen, or a ($C_1$–$C_4$)alkyl group, and R' is hydrogen, halogen, or a ($C_1$–$C_4$)alkyl group, provided that when Y is methyl or ethyl then both R and R' may not be hydrogen.

By a substituted alkyl group is meant an alkyl group having one or more of its hydrogen atoms replaced by another substituent group. Examples of the substituted alkyl groups which characterize 3-isothiazolones of this invention include hydroxyalkyl, haloalkyl, cyanoalkyl, alkylaminoalkyl, dialkylaminoalkyl, arylaminoalkyl, carboxyalkyl, carbalkoxyalkyl, alkoxyalkyl, aryloxyethyl, alkylthioalkyl, arylthioalkyl, haloalkoxyalkyl, cycloalkylaminoalkyl, such as morpholinoalkyl, piperidinoalkyl, pyrrolidonylalkyl, and the like, carbamoxyalkyl, alkenyl, haloalkenyl, alkynyl, haloalkynyl, isothiazolonylalkyl, and the like.

By a substituted aralkyl group is meant an aralkyl group having one or more of the hydrogen atoms on either the aryl ring or the alkyl chain replaced by another substituent group. Examples of the substituted aralkyl groups which characterize 3-isothiazoles of this invention include halogen-, lower alkyl-, or lower alkoxy-substituted aralkyl groups and the like.

By a substituted aryl group is meant an aryl group, such as benzene, naphthalene, or pyridine, having one or more of the hydrogen atoms on the aryl ring replaced by another substituent group. Examples of such substituent groups include halogen, nitro, lower alkyl, lower alkylacrylamino, lower carbalkoxy, sulfamyl, and the like.

The isothiazolones described above can form novel acid salts which also exhibit biocidal activity. Preparation of these biocidally active salts is readily achieved by reacting the above designated 3-isothiazolones with a strong inorganic or organic acid. Typical strong acids include hydrochloric, nitric, sulfuric, hydrobromic, chlorosulfuric, chloroacetic, oxalic, maleic, succinic, p-toluenesulfonic, and the like. Separation of the acid salts from the reaction medium is accomplished by any convenient means known to one skilled in the art.

Representative Y substituents include methyl, ethyl, propyl, isopropyl, butyl, hexyl, octyl, decyl, pentadecyl, octadecyl, cyclopropyl, cyclohexyl, benzyl, 3,4-dichlorobenzyl, 4-methoxybenzyl, 4-chlorobenzyl, 3,4-dichlorophenyl, hydroxymethyl, chloromethyl, chloropropyl, diethylaminoethyl, cyanomethyl, carbomethoxyethyl, ethoxyethyl, 2-methoxy-1-bromoethyl, 3,3,5-trimethylcyclohexyl, phenoxyethyl, p-chloroanilinomethyl, phenylcarbamoxymethyl, allyl, propynyl, vinyl, carboxyethyl, 1-isothiazolonylethyl, and 1,2,2,-trichlorovinyl.

Representative R substituents include hydrogen, bromo, chloro, iodo, methyl, ethyl, propyl, isopropyl, butyl and t-butyl.

Representative R' substituents are hydrogen, chloro, bromo, iodo, methyl, ethyl, propyl, isopropyl, butyl, t-butyl, chloromethyl, chloropropyl, bromomethyl, bromoethyl, and bromopropyl.

Typical compounds within the scope of Formula I include the following:
2-propyl-3-isothiazolone,
2-butyl-3-isothiazolone,
2-t-octyl-3-isothiazolone,
2-decyl-3-isothiazolone,
2-octyldecyl-3-isothiazolone,
2-cyclohexyl-3-isothiazolone,
4-chloro-2-methyl-3-isothiazolone,
4-bromo-2-methyl-3-isothiazolone,
5-chloro-2-methyl-3-isothiazolone,
5-chloro-2,4-dimethyl-3-isothiazolone,
4-bromo-5-chloro-2-methyl-3-isothiazolone,
4-bromo-2-cyclohexyl-3-isothiazolone,
4,5-dichloro-2-ethyl-3-isothiazolone,
4-methyl-2-octyl-3-isothiazolone,
4,5-dimethyl-2-octyl-3-isothiazolone,
2-benzyl-3-isothiazolone,
2-benzyl-4,5-dichloro-3-isothiazolone,
2-benzyl-5-chloro-3-isothiazolone,
2-(2',4'-dichlorobenzyl)-3-isothiazolone
2-(4'-methoxybenzyl)-3-isothiazolone
2-(4'-ethylbenzyl)-3-isothiazolone
2-(3',4'-dichlorophenyl)-3-isothiazolone,
2-(3',4'-dichlorophenyl)-4-methyl-3-isothiazolone,
2-(2-cyanoethyl)-3-isothiazolone,
2-(2-carbomethoxyethyl)-3-isothiazolone,
2-carbomethoxymethyl-3-isothiazolone,
2-(2-ethoxyethyl)-3-isothiazolone,
2-(3',3',5'-trimethylcyclohexyl)-3-isothiazolone,
2-(2-phenoxyethyl)-3-isothiazolone,
2-(2-methoxyethyl)-3-isothiazolone,
2-(3',4'-dichloroanilinomethyl)-3-isothiazolone,
2-(4'-chloroanilinomethyl)-3-isothiazolone,
2-(4'-nitroanilinomethyl)-3-isothiazolone,
2-morpholinomethyl-3-isothiazolone,
2-piperidinomethyl-3-isothiazolone,
2-phenylcarbamoxymethyl-3-isothiazolone, 2-(3'-chlorophenylcarbamoxymethyl)-3-isothiazolone,
2-(3',4'-dichlorophenylcarbamoxymethyl)-3-isothiazolone,
2-allyl-3-isothiazolone,
2-propynyl-3-isothiazolone,
2-vinyl-3-isothiazolone,
5-chloro-2-vinyl-3-isothiazolone,
2-methoxymethyl-3-isothiazolone,
2-(2-carboxyethyl)-3-isothiazolone,
2-(2-carb-n-butoxyethyl)-3-isothiazolone,
2-[1-(N-pyrrolidonyl)ethyl]-3-isothiazolone,
2-[1-(N-isothiazolonyl)ethyl]-3-isothiazolone,
2-(1,2,2-trichlorovinyl)-3-isothiazolone,
2-(1-bromo-2-methoxyethyl)-3-isothiazolone,
2-(2-chloroethyl)-3-isothiazolone,
2-(3-chloropropyl)-3-isothiazolone,
2-cyclopropyl-3-isothiazolone,
2-[2-(4'-chlorophenyl)ethyl]-3-isothiazolone,
2-n-hexyl-3-isothiazolone,
2-n-heptyl-3-isothiazolone,
2-cyclopentyl-3-isothiazolone,
2-(4'-chlorophenyl)-3-isothiazolone,
2-(2',4'-dichlorophenyl)-3-isothiazolone,
2-(2',3'-dichlorophenyl)-3-isothiazolone,
2-(2',5'-dichlorophenyl)-3-isothiazolone,
2-(3'-chlorophenyl)-3-isothiazolone,
2-phenyl-3-isothiazolone,
2-(2'-chlorophenyl)-3-isothiazolone,
2-n-pentyl-3-isothiazolone,
2-i-propyl-3-isothiazolone,
2-(2-hydroxyethyl)-3-isothiazolone,
2-(2-bromoethyl)-3-isothiazolone,
2-(1,2,2,2-tetrachloroethyl)-3-isothiazolone,
2-chloromethyl-3-thiazolone,
2-(2-dimethylaminoethyl)-3-isothiazolone,
4,5-dichloro-2-t-octyl-3-isothiazolone,
4-chloro-2-n-octyl-3-isothiazolone,
4-bromo-2-n-octyl-3-isothiazolone,
4-bromo-2-(4'-chlorophenyl)-3-isothiazolone,
4-bromo-2-t-butyl-3-isothiazolone,
2-(2,2,2-trichloro-1-hydroxyethyl)-3-isothiazolone,
2-(2,2,2-tribromo-1-hydroxyethyl)-3-isothiazolone,
2-trichlorobenzyl-3-isothiazolone,
2-sec-butyl-3-isothiazolone,
4-methyl-2-isopropyl-3-isothiazolone,
2-(4'-methylphenyl)-3-isothiazolone,
2-hydroxymethyl-3-isothiazolone, and
2-[2-(N,N-diethylamino)ethyl]-3-isothiazolone.

All of the isothiazolones with the exception of the hydroxyalkyl, alkenyl, and alkynyl derivatives, can be prepared by the cyclization of a substituted disulfide-amide having the formula

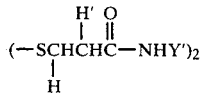

wherein H and H' are hydrogen or lower alkyl and Y' can be any of the groups embraced by Y in Formula I, as defined above, except alkenyl, alkynyl, and lower hydorxyalkyl groups. The cyclization is accomplished by reacting the disulfide-amide with a halogenating agent. Any halogenating agent may be employed in this reaction. Typical halogenating agents include chlorine, bromine, sulfuryl chloride, sulfuryl bromide, N-chlorosuccinimide, H-bromosuccinimide, iodine monochloride, and the like. Bromine and chlorine are preferred halogenating agents. Cyclization of the disulfide-amide will take place when 3 mole equivalents of halogenating agent are employed in the reaction. By providing an excess of halogenating agent, the isothiazolone may be halogenated at the 4- and/or 5-positions of Formula I. Where 5 mole equivalents of halogenating agent are available, mono-halogenation can take place. For di-halogenation, 7 mole equivalents of halogenating agent are required. Preparation of isothiazolones having the 4- and 5-positions substituted with different halogens is achieved by the halogenation of an isothiazolone already halogenated at one of the two positions. For example, if a 4-bromo-5-chloro-3-isothiazolone is desired, it can be obtained by bromination of a 5-chloro-3-isothiazolone or the chlorination of a 4-bromo-3-isothiazolone. The starting 3-isothiazolone is prepared by the cyclization of a disulfideamide as described above. The cyclization process will proceed over a broad temperature range and temperature is not critical to the reaction. Generally, the cyclization will be carried out in the range of 0° to 100° C. The reaction is carried out in an inert non-aqueous solvent, such as, for example, benzene, toluene, xylene, ethyl acetate, or ethylene dichloride. In addition, the 4,5-dihalo-3-isothiazolones may be prepared by in situ halogenation of a 5-halo-3-isothiazolone, as described for type A compounds.

In addition, isothiazolones of the formula

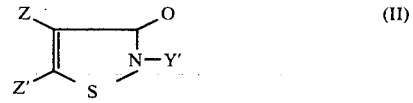

can be prepared by the method of Goerdeler and Mittler as described in *Chem. Ber.*, 96, 944–954 (1963). In Formula II, Y' can be any of the groups embraced by Y in Formula I, as defined above, except alkenyl, alkynyl, and lower hydroxyalkyl groups, Z is hydrogen or lower alkyl and Z' is lower alkyl, This preparation involves the halogenation of a substituted β-thioketoamide in an inert organic ester solvent, such as ethyl acetate. The β-thioketoamide can be represented by the formula

wherein Z, Z' and Y' are as defined above.

Another process for preparing some of the compounds of this invention is that of Crow and Leonard as set forth in the *Journal of Organic Chemistry*, 30, 2660–2665 (1965). This method entails the converting of a β-substituted thiocyanoacrylamide or thiosulfatoacrylamide to the isotniazolone. This reaction may be represented by the following equation:

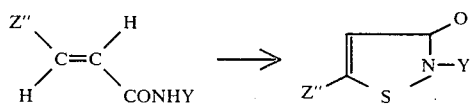

wherein Y is as defined in Formula I, Z" is hydrogen or lower alkyl and N is —SCN or —S₂O₃⁻. Generally, conversion of the substituted thiocyanoacrylamide or thiosulfato acrylamide to the isothiazolone is achieved by the treating the amide with an acid, such as for example, sulfuric acid. However, when N is SCN, transition metal salts, such as nickel sulfate, ferrous sulfate, ferric sulfate, copper sulfate and the like, can also be readily utilized, and when N is $S_2O_3^\ominus$, iodine can be used. Preparation of the thiocyanoacrylamide and thiosulfatoacrylamide as taught by Crow and Leonard involves the reacting of a substituted propiolamide with thiocyanic acid or thiosulfate.

Some of the 2-hydroxyalkyl-3-isothiazolone derivatives disclosed herein are obtained by reacting formaldehyde or an alkylene oxide, such as ethylene oxide, propylene oxide and the like, with a 3-hydroxyisothiazole. This reaction can be carried out in water, alcohols, or non-hydroxylic solvents, such as benzene, toluene, ethyl acetate, ether, and hexane, and preferably a reaction temperature of about −20° C. to 100° C. is chosen. In order to facilitate the reaction, a basic catalyst, such as potassium carbonate, calcium carbonate, potassium hydroxide, or sodium hydroxide, can be advantageously employed.

Preparation of the 2-haloalkyl-3-isothiazolones of the invention can be accomplished by reacting a 2-hydroxyalkyl-3-isothiazolone with a halogen compound such as thionyl chloride, phosphorus tribromide, phosphorus trichloride and the like. Either the halogen compound or a non-hydroxylic solvent can be used as a solvent for the reaction, which will generally be carried out at about −20° C. to 100° C.

Some of the 2-alkylamino and 2-arylamino-3-isothiazolones of the invention can be obtained by reacting formaldehyde and an appropriate amine with a 3-hydroxyisothiazole. An equimolar ratio of the reactants is generally used, and water, alcohols, or non-hydroxylic solvents can be employed. The reaction proceeds smoothly over a temperature range of about −20° C. to 100° C.

The 2-carbamoxyalkyl-3-isothiazolones of the invention are obtained by reacting an isocyanate with a 2-hydroxyalkyl-3-isothiazolone. Although an equimolar ratio of reactants is generally used, an excess of the isocyanate can be used. Non-hydroxylic solvents, such as aromatic and aliphatic hydrocarbons and chlorinated hydrocarbons, ethers, esters, nitriles, and amides can be used in carrying out the reaction. A temperature of about −20° C. to 80° C. is usually chosen for the reaction, and when higher molecular weight or more complex isocyanates are used as reactants, a catalyst, such as a tertiary amine, can be advantageously employed to facilitate reaction.

The 2-alkenyl and 2-alkynyl-3-isothiazolones of the invention can be prepared by reacting an appropriate haloalkene or haloalkyne with a 3-hydroxyisothiazole. The reaction can be carried out in water, alcohols, and non-hydroxylic solvents and a temperature of about −10° C. to 100° C. is generally utilized. An acid-accepting base, such as a metal hydride, a metal hydroxide, or a tertiary amine, is also generally used to catalyze the reaction.

The 2-vinyl-3-isothiazolones of the invention are prepared by reacting a vinyl acetate with a 3-hydroxyisothiazole. The vinyl acetate or other non-hydroxylic compounds can be used as a solvent for the reaction which can be carried out at a temperature of about −10° C. to 100° C. Mercuric salts can be advantageously used to catalyze the reaction.

Various 3-isothiazolone derivatives can be obtained by the reactive addition of a vinyl compound having the formula $CH_2=CH-Q$ with a 3-hydroxyisothiazole. Q can represent groups such as N-pyrrolidonyl, N-isothiazolonyl, and the like. The addition is generally carried out at a temperature of about −20° C. to 100° C. using water, alcohols, or non-hydroxylic compounds as solvents. For sluggish reactants, a basic catalyst, such as a tertiary amine or a quaternary hydroxide can be used to aid the reaction.

The 2-(2,2,2-trihalo-1-hydroxyalkyl)-3-isothiazolones of the invention are prepared by reacting a trihaloacetaldehyde with a 3-hydroxyisothiazole, in water, alcohols, or non-hydroxylic compounds as solvents, at a temperature of about −10° C. to 100° C. These isothiazolones can be dehydrated to form the corresponding unsaturated 2-(1,2,2-trihaloalkenyl)-3-isothiazolones by reacting them with a thionyl halide.

By way of demonstration, the following examples are offered to illustrate this invention and are not to be construed as limitations thereof. In Table I, the compounds prepared by the above-described processes and constituting Examples 1 through 103 are named and their embodiments indicated. Table II lists the elemental analyses and melting points (or boiling ranges) for the examples previously described in Table I. Specific illustrative preparations of Examples 7, 9, 11, 15, 16, 37, 38, 52, 57, 60, 62, 67, and 98 are set forth below.

EXAMPLE 7

Preparation of 5-chloro-2-methyl-3-isothiazolone

To an ethylene dichloride (1 liter) slurry of dithio-N,N'-dimethyldipropionamide, 70.9 g (0.3 mole), there was added at 10°–15° C. over 1.5 hour 121.5 g. (0.9 mole) of sulfuryl chloride. After addition, the reaction slurry was allowd to warm to 20°–25° C. and stirred overnight to assure completion of the reaction. The slurry was then filtered to give 37.1 g. of 2-methyl-3-isothiazolone hydrochloride. The ethylenedichloride filtrate, upon evaporation to approximately one-half volume, yielded an additional quantity (30.5 g.) of less pure hydrochloride. Complete evaporation of the ethylene dichloride filtrate gave 24.7 g. of oily residue which upon sublimation at 0.1 mm. (40°–60° C.) gave 11.5 g. of 5-chloro-2-methyl-3-isothiazolone, m.p. 44°–47° C.

EXAMPLE 9

Preparation of 4,5-dichloro-2-methyl-3-isothiazolone

To a solution of 5.2 g. (0.045 mole) of 2-methyl-3-isothiazolone in 100 ml. of ethyl acetate at −70° C. was added 6.08 g. (0.045 mole) of sulfuryl chloride over 45 min. The reaction was stirred at this temperature for 4 hours, then was allowed to come to room temperature. The ethyl acetate was removed by evaporation from the resulting slurry, and the solid thus obtained was extracted with benzene. Filtration and evaporation of the benzene gave 4 g. (96% based upon sulfuryl chloride) of 4,5-dichloro-2-methyl-3-isothiazolone, which upon crystallization from ligroin (90°–120°) gave pure material, m.p. 114°–17°.

EXAMPLE 11

Preparation of 4-methyl-2-(3,4-dichlorophenyl)-3-isothiazolone

Dithio-(3',4'-dichloro)-diisobutyranilide, 12.8 g. (0.0234 mole), was slurried in 250 ml. of ethylene dichloride, and a solution of 9.5 g. (0.0702 mole) of sulfuryl chloride in 25 ml. of ethylene dichloride was added dropwise at 25°–30° C. over one hour. The slurry was stirred overnight to insure completion of the reaction and then filtered to give 8.6 g. of gray 2-(3,4-dichlorophenyl)-4-methyl-3-isothiazolone, m.p. 160°–161° C. The product was crystallized from ethyl acetate to give a m.p. of 161°–163° C.

EXAMPLE 15

Preparation of 4-bromo-2-methyl-3-isothiazolone

To a solution of 5 g. (0.043 mole) of 2-methyl-3-isothiazolone in 100 ml. of ethylene dichloride at 0°–5° was added dropwise over a period of 35 min. a solution of 6.54 g (0.043 mole) of bromine in 25 ml. of ethylene dichloride. When the addition was complete the mixture was allowed to warm to room temperature and stir overnight. The mixture was filtered giving 1.6 g. (14%) of 4-bromo-2-methyl-3-isothiazolone hydrobromide as red solid. The hydrobromide was dissolved in water and extracted continuously with ether. Evaporation of the extract gave 1.3 g. of 4-bromo-2-methyl-3-isothiazolone, m.p. 94–97 from ligroin (90°–120°). NMR analysis of this bromo compound confirmed its structure as the 4-bromo isomer by the 5-H absorption at 1.87 ↑ and showed no absorption for a 4 proton.

EXAMPLE 16

Preparation of 2-hydroxymethyl-3-isothiazolone

Aqueous formaldehyde (37 percent), 4.5 g. (0.056 mole) was diluted with 25 ml. of water, and then 3.8 g. (0.023 mole) of potassium carbonate was added. Thereafter, 5.5 g. (0.055 mole) of 3-hydroxyisothiazole was added to the formaldehyde solution in one portion. A solid precipitate soon formed, and after 2 hours stirring, was filtered off to yield 1.8 g. of white solid 2-hydroxymethyl-3-isothiazolone.

EXAMPLE 37

Preparation of 4-chloro-2-t-octyl-3-isothiazolone

To a solution of 10.7 g. (0.05 mole) of 2-t-octyl-3-isothiazolone in 100 ml. of chloroform was added in a single portion 13.3 g. (0.1 mole) of N-chlorosuccinimide. The mixture warmed somewhat but did not require cooling. After stirring for 2.5 hours the mixture was filtered giving 7.5 g. of crude succinimide. The filtrate was evaporated under reduced pressure and the residue dissolved in ether. The other solution was extracted with water, dried over anhydrous magnesium sulfate, and evaporated to a mixture of solid and oil. The oil was washed from the solid with hexane leaving 1.7 g. (14%) of white 4-chloro-2-t-octyl-3-isothiazolone, m.p. 137–140.

NMR analysis confirmed the 4-chloro structure of 4-chloro-2-t-octyl-3-isothiazolone by the 5-H absorption at 2.18 ↑.

EXAMPLE 33

Preparation of 4-bromo-2-t-octyl-3-isothiazolone

To a solution of 10.7 g. (0.05 mole) of 2-t-octyl-3-isothiazolone in 100 ml. of chloroform was added in a single portio 17.8 g. (0.1 mole) of N-bromosuccinimide, and a slight exotherm was observed. After stirring for 3 hours the mixture was filtered, and the solid washed with ether. The chloroform filtrate and ether washings were then evaporated to give a total of 7.8 g. (54%) of 4-bromo-2-t-octyl-3-isothiazolone, m.p. 133–142. NMR analysis of this product showed 5-H absorption. at 2.00 ↑, with no observable 4-H present.

EXAMPLE 52

Preparation of 2-(3',4'-dichloroanilinomethyl-3-isothiazolone

A 5.0 gm. (0.05 mole) sample of 3-isothiazolone and 8.3 gm. (0.05 mole) of 3,5-dichloroaniline were dissolved in 7.0 ml. methanol. The solution was cooled to 10° C. and 0.05 mole of aqueous formaldehyde solution was slowly added. The mixture was cooled to 0° C., and the precipitated white solid was filtered off to give 8.9 g. (65%) of 2-(3',4'-dichloroanilinomethyl)-3-isothiazolone, m.p. 120°–2° C.

EXAMPLE 57

Preparation of 2-N-phenylcarbamoxymethyl-3-isothiazolone

In 50 ml. of benzene was mixed 5.25 g. (0.04 mole) of 2-hydroxymethyl-3-isothiazolone and 4.75 g. (0.04 mole) of phenylisocyanate. A few drops of triethylamine were added, and the mixture was heated at 50° C. for five hours. The white precipitate was then filtered off, washed with benzene, and dried to give 3.3 g. (30%) of 2-N-phenylcarbamoxymethyl-3-isothiazolone, m.p. 189°–90° from ethyl acetate.

EXAMLE 60

Preparation of 2-allyl-3-isothiazolone

To a solution of 20.2 g. (0.20 mole) of 3-hydroxyisothiazole in 100 ml. of methanol was added at 25° C. 47.5 g. (0.22 mole) of sodium methoxide (25% in methanol). To the resulting solution was then added dropwise 24.2 g. (0.20 mole) of allyl bromide in 50 ml. of methanol. After stirring for several hours, the methanol was removed by distillation, and the residue was taken up in ether. After washing with water, the ether was dried and removed under vacuum. The crude oil residue was then distilled to give 2.8 g. (10%) of 2-allyl-3-isothiazolone, b.p. 75° C. (0.25 mm).

EXAMPLE 62

Preparation of 2-vinyl-3-isothiazolone

In 300 ml. of vinyl acetate was dissolved 5.0 g. of mercuric acetate by gentle refluxing. The solution was then cooled to 0° C. and 0.4 ml. of 30% fuming sulfuric acid was added, followed by 20 g. (0.20 mole) of 3-hydroxyisothiazole. During five days the solution was heated at 50° C. The solution was then cooled and 4.5 g. of sodium acetate was added. After stirring for three hours, the mixture was filtered, and the excess vinyl acetate was removed under vacuum. Distillation of the residue gave 11.3 g. (45%) of 2-vinyl-3-isothiazolone, b.p. 90–94 (0.05 mm). The distilled product solidified and after crystallization from ether-hexane had m.p. 56°–58° C.

EXAMPLE 67

Preparation of 2-{1-[1-(2-pyrrolidononyl)]ethyl}-3-isothiazolone

To a solution of 10.1 g. (0.10 mole) of 3-hydroxyisothiazole in 50 ml. of benzene was added 11.1 g. (0.10 mole) of 1-vinyl-pyrrolidinone. A slight exotherm was observed and after stirring at 25° C. for 12 hours, a white precipitate had formed. After filtration and drying, 11.5 g. (54%) of 2-{1-[1-(2-pyrrolidinonyl)]-ethyl}-3-isothiazolone, m.p. 85°–88° C., was obtained.

EXAMPLE 98

Preparation of 2-(1-hydroxy-2,2,2-trichloroethyl)-3-isothiazolone

To a solution of 5.0 g. (0.05 mole) of 3-hydroxyisothiazole in 50 ml. of benzene was added at 25° C. over 0.5 hour 7.8 g. (0.05 mole) of chloral in 15 ml. of benzene. A white precipitate formed, and after two hours stirring at 25° C., the reaction was filtered to give 11.5 g. (90%) of 2-(1-hydroxy-2,2,2-trichloroethyl)-3-isothiazolone, m.p. 117°–18° C. from ether-hexane.

TABLE I

3-ISOTHIAZOLONE EXAMPLES

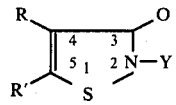

| Example No. | R | R' | Y | Name |
|---|---|---|---|---|
| 1 | H | H | $-C_3H_7-n$ | 2-n-propyl-3-isothiazolone |
| 2 | H | H | $-C_4H_9-t$ | 2-t-butyl-3-isothiazolone |
| 3 | H | H | $-C_4H_9-n$ | 2-n-butyl-3-isothiazolone |
| 4 | H | H | $-C_6H_{11}$ | 2-cyclohexyl-3-isothiazolone |
| 5 | H | H | $-C_8H_{17}-t$ | 2-t-octyl-3-isothiazolone |
| 6 | H | H | $-CH_2C_6H_4$ | 2-benzyl-3-isothiazolone |
| 7 | H | Cl | $-CH_3$ | 5-chloro-2-methyl-3-isothiazolone |
| 8 | H | Cl | $-CH_2C_6H_4$ | 5-chloro-2-benzyl-3-isothiazolone |
| 9 | Cl | Cl | $-CH_3$ | 4,5-dichloro-2-methyl-3-isothiazolone |
| 10 | $CH_3$ | H | $-CH_3$ | 2,4-dimethyl-3-isothiazolone |
| 11 | $CH_3$ | H | $-C_6H_3Cl_2-3,4$ | 4-methyl-2-(3,4-dichlorophenyl)-3-isothiazolone |
| 12 | H | H | $-C_6H_3Cl_2-3,4$ | 2-(3,4-dichlorophenyl)-3-isothiazolone |
| 13 | Cl | Cl | $-CH_2C_6H_5$ | 4,5-dichloro-2-benzyl-3-isothiazolone |
| 14 | Br | Cl | $-CH_3$ | 4-bromo-5-chloro-2-methyl-3-isothiazolone |
| 15 | Br | H | $-CH_3$ | 4-bromo-2-methyl-3-isothiazolone |
| 16 | H | H | $-CH_2CH$ | 2-hydroxymethyl-3-isothiazolone |
| 17 | H | H | $-CH_2CH_2N(CH_2CH_3)_2$ | 2-($\beta$-diethylaminoethyl)-3-isothiazolone |
| 18 | H | H | $-C_3H_7 \cdot HCl$ | 2-n-propyl-3-isothiazolone hydrochloride |
| 19 | H | Cl | $-CH_3 \cdot HCl$ | 5-chloro-2-methyl-3-isothiazolone hydrochloride |
| 20 | H | H | $-C_2H_5 \cdot HCl$ | 2-ethyl-3-isothiazolone hydrochloride |
| 21 | H | H | $-CH_3 \cdot HCl$ | 2-methyl-3-isothiazolone hydrochloride |
| 22 | H | H | $-CH_2C_6H_5 \cdot HCl$ | 2-benzyl-3-isothiazolone hydrochloride |
| 23 | H | H | $-C_{12}H_{25}-n$ | 2-n-dodecyl-3-isothiazolone |
| 24 | H | H | $-C_{14}H_{29}-n$ | 2-n-tetradecyl-3-isothiazolone |
| 25 | H | H | $-CH_2-C_6H_4-Cl-4$ | 2-(4-chlorobenzyl)-3-isothiazolone |
| 26 | H | H | $-CH_2-C_6H_4-Cl-2$ | 2-(2-chlorobenzyl)-3-isothiazolone |
| 27 | H | H | $-CH_2-C_6H_3-Cl_2-2,4$ | 2-(2,4-dichlorobenzyl)-3-isothiazolone |
| 28 | H | H | $-CH_2-C_6H_3-Cl_2-3,4$ | 2-(3,4-dichlorobenzyl)-3-isothiazolone |
| 29 | H | H | $-CH_2-C_6H_4-OCH_3-n$ | 2-(4-methoxybenzyl)-3-isothiazolone |
| 30 | H | H | $-CH_2-C_6H_4-CH_3-4$ | 2-(4-methylbenzyl)-3-isothiazolone |
| 31 | H | H | $-CH_2-CH(-C_4H_9)C_2H_5$ | 2-(2-ethylhexyl)-3-isothiazolone |
| 32 | H | H | $-CH_2CH_2-C_6H_5$ | 2-(2-phenylethyl)-3-isothiazolone |
| 33 | H | Cl | $-CH_2CH_2-C_6H_5$ | 2-(2-phenylethyl)-5-chloro-3-isothiazolone |
| 34 | H | H | $-CH(CH_3)C_6H_5$ | 2-(1-phenylethyl)-3-isothiazolone |
| 35 | H | H | $-C_{10}H_{21}-n$ | 2-n-decyl-3-isothiazolone |
| 36 | H | H | $-C_8H_{17}-n$ | 2-n-octyl-3-isothiazolone |
| 37 | Cl | H | $-C_8H_{17}-t$ | 2-t-octyl-4-chloro-3-isothiazolone |
| 38 | Br | H | $-C_8H_{17}-t$ | 2-t-octyl-4-bromo-3-isothiazolone |
| 39 | H | H | $-C_9H_{19}-n$ | 2-n-nonyl-3-isothiazolone |
| 40 | H | Cl | $-C_8H_{17}-n$ | 2-n-octyl-5-chloro-3-isothiazolone |
| 41 | H | H | $-C_6H_4NO_2-4$ | 2-(4-nitrophenyl)-3-isothiazolone |
| 42 | H | H | $-C_6H_4COOC_2H_5-4$ | 2-(4-carbothoxyphenyl)-3-isothiazolone |
| 43 | H | H | $-CH_2CH_2CN$ | 2-(2-cyanoethyl)-3-isothiazolone |
| 44 | H | H | $-CH_2CH_2CO_2CH_3$ | 2-(2-carbomethoxyethyl)-3-isothiazolone |
| 45 | H | H | $-CH_2CH_2CO_2CH_3 \cdot HCl$ | 2-(2-carbomethoxyethyl)-3-isothiazolone hydrochloride |
| 46 | H | H | $-CH_2CO_2CH_3 \cdot HCl$ | 2-carbomethoxymethyl-3-isothiazolone hydrochloride |
| 47 | H | H | $-CH_2CH_2OCH_2CH_3 \cdot HCl$ | 2-(2-ethoxyethyl)-3-isothiazolone hydrochloride |
| 48 | H | H | $-CH_2CH_2OCH_2CH_3$ | 2-(2-ethoxyethyl)-3-isothiazolone |
| 49 | H | H | (3,3,5-trimethylcyclohexyl group) | 2-(3',3',5'-trimethylcyclohexyl)-3-isothiazolone |
| 50 | H | H | $-CH_2CH_2OC_6H_5$ | 2-(2-phenoxyethyl)-3-isothiazolone |
| 51 | H | H | $-CH_2CH_2OCH_3$ | 2-(2-methoxyethyl)-3-isothiazolone |
| 52 | H | H | $-CH_2NHC_6H_3-Cl_2-3,4$ | 2-(3',4'-dichloroanilinomethyl)-3-isothiazolone |
| 53 | H | H | $-CH_2NHC_6H_4-Cl-4$ | 2-(4'-chloroanilinomethyl)-3-isothiazolone |
| 54 | H | H | $-CH_2NHC_6H_4 \cdot NO_2-4$ | 2-(4'-nitroanilinomethyl)-3-isothiazolone |
| 55 | H | H | $-CH_2-N$(morpholino) | 2-morpholinomethyl-3-isothiazolone |

TABLE I-continued

3-ISOTHIAZOLONE EXAMPLES

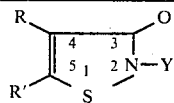

| Example No. | R | R' | Y | Name |
|---|---|---|---|---|
| 56 | H | H | —CH₂—N(piperidine) | 2-piperidinomethyl-3-isothiazolone |
| 57 | H | H | —CH₂OCONHC₆H₅ | 2-phenylcarbamoxymethyl-3-isothiazolone |
| 58 | H | H | —CH₂OCONHC₆H₄—Cl—3 | 2-(3'-chlorophenylcarbamoxymethyl)-3-isothiazolone |
| 59 | H | H | —CH₂OCONHC₆H₃—Cl₂—3,4 | 2-(3',4'-dichlorophenylcarbamoxymethyl)-3-isothiazolone |
| 60 | H | H | —CH₂CH=CH₂ | 2-allyl-3-isothiazolone |
| 61 | H | H | —CH₂C≡CH | 2-propynyl-3-isothiazolone |
| 62 | H | H | —CH=CH₂ | 2-vinyl-3-isothiazolone |
| 63 | H | Cl | —CH=CH₂ | 5-chloro-2-vinyl-3-isothiazolone |
| 64 | H | H | —CH₂OCH₃ | 2-methoxymethyl-3-isothiazolone |
| 65 | H | H | —CH₂CH₂CO₂H . HCl | 2-(2-carboxyethyl)-3-isothiazolone hydrochloride |
| 66 | H | H | —CH₂CH₂CO₂C₄H₉—n | 2-(2-carb-n-butoxyethyl-3-isothiazolone |
| 67 | H | H | —CH(CH₃)—N(pyrrolidinone) | 2-[1-(N-pyrrolidonyl)ethyl]-3-isothiazolone |
| 68 | H | H | —CH(CH₃)—N(isothiazolone) | 2-[1-(N-isothiazolonyl)ethyl]-3-isothiazolone |
| 69 | H | H | —CCl=CCl₂ | 2-(1,2,2-trichlorovinyl)-3-isothiazolone |
| 70 | H | H | —CHBrCH₂OCH₃ | 2-(1-bromo-2-methoxyethyl)-3-isothiazolone |
| 71 | H | H | —CH₂CH₂Cl | 2-(2-chloroethyl)-3-isothiazolone |
| 72 | H | H | —CH₂CH₂Cl . HCl | 2-(2-chloroethyl)-3-isothiazolone hydrochloride |
| 73 | H | H | —CH₂CH₂CH₂Cl | 2-(3-chloropropyl)-3-isothiazolone |
| 74 | H | H | —cyclopropyl | 2-cyclopropyl-3-isothiazolone |
| 75 | H | H | —CH₂CH₂C₆H₅—Cl—4 | 2-[2-(4'-chlorophenyl)ethyl]-3-isothiazolone |
| 76 | H | H | —C₆H₁₃—n | 2-n-hexyl-3-isothiazolone |
| 77 | H | H | —C₇H₁₅—n | 2-n-heptyl-3-isothiazolone |
| 78 | H | H | —cyclopentyl | 2-cyclopentyl-3-isothiazolone |
| 79 | H | H | —C₆H₄—Cl—4 | 2-(4'-chlorophenyl)-3-isothiazolone |
| 80 | H | H | —C₆H₃—Cl₂—2,4 | 2-(2',4'-dichlorophenyl)-3-isothiazolone |
| 81 | H | H | —C₆H₃—Cl₂—2,3 | 2-(2',3'-dichlorophenyl)-3-isothiazolone |
| 82 | H | H | —C₆H₃—Cl₂—2,5 | 2-(2',5'-dichlorophenyl)-3-isothiazolone |
| 83 | H | H | —C₆H₄—Cl—3 | 2-(3'-chlorophenyl)-3-isothiazolone |
| 84 | H | H | —C₆H₅ | 2-phenyl-3-isothiazolone |
| 85 | H | H | —C₆H₄—Cl—2 | 2-(2'-chlorophenyl)-3-isothiazolone |
| 86 | H | H | —C₅H₄—n | 2-n-pentyl-3-isothiazolone |
| 87 | H | H | —C₃H₇—iso | 2-i-propyl-3-isothiazolone |
| 88 | H | H | —CH₂CH₂OH | 2-(2-hydroxyethyl)-3-isothiazolone |
| 89 | H | H | —CH₂CH₂Br . HBr | 2-(2-bromoethyl)-3-isothiazolone hydrobromide |
| 90 | H | H | —CHCl—CCl₃ | 2-(1,2,2,2-tetrachloroethyl)-3-isothiazolone |
| 91 | H | H | —CH₂Cl | 2-chloromethyl-3-isothiazolone |
| 92 | H | H | —CH₂N(CH₃)₂ | 2-(2-dimethylaminoethyl)-3-isothiazolone |
| 93 | Cl | Cl | —C₈H₁₇—t | 4,5-dichloro-2-t-octyl-3-isothiazolone |
| 94 | Cl | H | —C₈H₁₇—n | 4-chloro-2-n-octyl-3-isothiazolone |
| 95 | Br | H | —C₈H₁₇—n | 4-bromo-2-n-octyl-3-isothiazolone |
| 96 | Br | H | —C₆H₄—Cl—4 | 4-bromo-2-(4'-chlorophenyl)-3-isothiazolone |
| 97 | Br | H | —C₄H₉—t | 4-bromo-2-t-butyl-3-isothiazolone |
| 98 | H | H | —CHOH—CCl₃ | 2-(2,2,2-trichloro-1-hydroxyethyl)-3-isothiazolone |
| 99 | H | H | —CHOH—CBr₃ | 2-(2,2,2-tribromo-1-hydroxyethyl)-3-isothiazolone |
| 100 | H | H | —CH₂C₆H₂Cl₃ | 2-trichlorobenzyl-3-isothiazolone |
| 101 | H | H | —CH₂C₆H₄—OCH₃—4 . HCl | 2-(4'-methoxybenzyl)-3-isothiazolone hydrochloride |
| 102 | H | H | —C₄H₉—sec | 2-sec-butyl-3-isothiazolone |
| 103 | CH₃ | H | —C₃H₇—iso | 4-methyl-2-iso-propyl-3-isothiazolone |
| 104 | H | Cl | —C₈H₁₇—n | 5-chloro-2-n-octyl-3-isothiazolone |
| 105 | Cl | Cl | —C₆H₁₁ | 4,5-dichloro-2-cyclohexyl-3-isothiazolone |
| 106 | CH₃ | Cl | —C₆H₄Cl—3 | 5-chloro-2-(3-chlorophenyl)-4-methyl-3-isothiazolone |

TABLE II

| Example No. | Melting Point in °C. | ANALYSIS[1] | | | | |
|---|---|---|---|---|---|---|
| | | C | H | N | S | Cl or Br |
| 1 | 65–68 | 50.28(50.3) | 6.17(6.33) | 9.83(9.78) | 22.30(22.3) | |
| 2 | 75–79 | 46.76(53.5) | 6.76(7.06) | 8.42(8.92) | 16.43(20.4) | |
| 3 | 99 | 52.10(53.5) | 7.11(7.06) | 8.54(8.92) | 19.35(20.4) | |
| 4 | 109–111 | 58.96(59.0) | 7.20(7.10) | 7.59(7.65) | 17.41(17.5) | |
| 5 | 97–100 | 61.91(62.0) | 9.03(9.0) | 6.55(6.57) | 14.89(15.03) | |
| 6 | 78–80 | 62.82(62.8) | 4.84(4.7) | 7.22(7.3) | 16.97(16.75) | |
| 7 | 44–47 | 32.80(32.1) | 2.64(2.7) | 9.55(9.5) | 20.79(21.4) | 23.48(23.7) |
| 8 | 57–59 | 53.19(53.2) | 3.46(3.6) | 6.18(6.2) | 13.80(14.2) | 15.01(15.74) |
| 9 | 114–117 | 27.31(26.1) | 1.43(1.6) | 7.22(7.6) | 17.42(17.4) | 37.89(38.6) |
| 10 | 58–68 | 45.99(46.4) | 5.77(5.4) | 11.38(10.8) | 24.39(24.8) | |
| 11 | 161–163 | 45.92(45.8) | 2.88(2.7) | 5.59(5.35) | 11.91(12.2) | 26.93(27.1) |
| 12 | 131–133 | 43.95(43.9) | 1.95(2.05) | 5.66(5.69) | 13.09(13.0) | |
| 13 | 62–64 | 47.10(46.1) | 2.86(2.7) | 5.35(5.4) | 12.48(12.3) | 26.40(27.4) |
| 14 | 86–87 | 22.24(21.0) | 1.81(1.3) | 5.82(6.1) | 13.83(14.0) | 15.63(15.5) **32.78(34.9) |
| 15 | 94–97 | 25.68(24.7) | 1.75(2.0) | 7.22(7.2) | | **39.78(41.2) |
| 16 | 124–126 | 36.43(36.5) | 3.75(3.7) | 10.44(10.7) | 24.30(24.4) | |
| 17 | oil | 52.70(54.1) | 6.35(8.06) | 14.17(14.0) | 13.70(16.0) | N.E.$^a$ 216(200) |
| 18 | 87–90 | 38.64(40.2) | 5.88(5.61) | 7.50(7.79) | 16.85(17.83) | 17.85(19.7) |
| 19 | — | 25.78(25.8) | 3.17(2.7) | 7.07(7.5) | 14.9(17.2) | 32.83(38.1) |
| 20 | 144–146 | 36.44(36.3) | 4.80(4.8) | 8.30(8.5) | 19.20(19.3) | 21.27(21.5) |
| 21 | 162–166 | 30.76(31.8) | 4.27(4.0) | 8.89(9.3) | 20.79(21.2) | 22.24(23.5) |
| 22 | 147–153 | 52.78(52.8) | 4.60(4.39) | 6.33(6.51) | 14.21(14.1) | 15.64(15.6) |
| 23 | 46–49 | 66.98(66.9) | 9.90(10.0) | 5.25(5.2) | 11.72(11.90) | |
| 24 | 53–55 | 68.88(68.7) | 10.61(10.5) | 4.68(4.7) | 10.88(10.8) | |
| 25 | 87–88 | 52.78(53.2) | 3.54(3.6) | 6.02(6.3) | 14.59(14.2) | 15.75(15.7) |
| 26 | 99–100 | 53.39(53.2) | 3.69(3.6) | 6.18(6.3) | 13.95(14.2) | 15.96(15.7) |
| 27 | 122–124 | 46.18(46.2) | 2.80(2.7) | 5.25(5.4) | 12.46(12.3) | 26.85(27.3) |
| 28 | 87–89 | 45.87(46.2) | 2.62(2.7) | 5.15(5.4) | 12.12(12.3) | 27.33(27.3) |
| 29 | 80–82 | 59.74(59.7) | 4.96(5.0) | 6.25(6.3) | 14.58(14.5) | |
| 30 | 76–77 | 64.60(64.4) | 5.32(5.4) | 6.60(6.8) | 15.60(15.6) | |
| 31 | 119–120 (.005mm)* | 60.81(62.0) | 8.88(8.9) | 6.46(6.6) | 14.70(15.0) | |
| 32 | 76–78 | 64.35(64.5) | 5.49(5.4) | 6.75(6.8) | 15.40(15.6) | |
| 33 | 55–59 | 55.22(55.2) | 3.95(4.2) | 5.62(5.9) | 13.16(13.4) | 14.51(14.8) |
| 34 | 138–140 (.003mm)* | 62.52(64.5) | 5.27(5.4) | 6.45(6.8) | 14.10(15.6) | |
| 35 | 41–42 | 64.80(64.7) | 9.31(9.6) | 5.46(5.8) | 13.49(13.2) | |
| 36 | 120(0.01mm)* | 62.00(62.0) | 8.81(8.9) | 6.48(6.6) | 14.89(15.0) | |
| 37 | 137–140 | 52.38(53.5) | 7.81(7.3) | 5.62(5.7) | — | 12.19(14.5) |
| 38 | 138–142 | 44.76(45.2) | 6.48(6.2) | 4.58(4.8) | 10.82(11.0) | **25.8(27.4) |
| 39 | 30–31 | 63.34(63.45) | 9.40(9.29) | 6.08(6.17) | 13.97(14.10) | |
| 40 | oil | 55.05(53.4) | 7.76(7.3) | 5.76(5.7) | — | 11.13(14.35) |
| 41 | 170–175 dec. | 48.62(48.7) | 2.78(2.72) | 12.77(12.60) | — | |
| 42 | 141–142 | 58.12(57.8) | 4.46(4.44) | 5.70(5.62) | 12.79(12.85) | |
| 43 | 85–6 | 46.68(46.8) | 3.92(3.93) | 18.25(18.2) | 20.20(20.8) | |
| 44 | 125(0.01mm)* | 44.69(44.9) | 4.92(4.81) | 7.41(7.49) | 17.02(17.1) | |
| 45 | | 37.81(37.6) | 4.60(4.48) | 6.21(6.26) | 14.25(14.3) | 14.64(15.9) |
| 46 | 90–93 | 34.39(34.4) | 3.69(3.85) | 6.81(6.68) | 15.08(14.8) | 16.30(16.9) |
| 47 | 99–103 | 40.11(39.9) | 5.98(6.17) | 6.62(6.65) | 15.32(15.4) | 15.37(16.9) |
| 48 | 90(0.04mm)* | 48.95(48.8) | 6.42(6.4) | 7.98(8.1) | 18.16(18.4) | |
| 49 | | 63.61(64.0) | 8.45(8.50) | 6.12(6.22) | 14.19(14.2) | |
| 50 | 78–81 | 59.61(59.7) | 5.15(5.3) | 6.23(6.3) | 14.28(14.5) | |
| 51 | 89–112 (0.05mm)* | 44.82(45.3) | 5.77(5.69) | 8.66(8.79) | 20.05(20.1) | |
| 52 | 120–122 | 43.75(43.6) | 3.10(2.92) | 10.18(10.2) | 11.70(12.0) | 25.69(25.7) |
| 53 | 93–94 | 49.74(49.7) | 3.81(3.75) | 11.59(11.6) | 13.28(13.3) | |
| 54 | 196–197 | 47.74(47.7) | 3.56(3.60) | 16.66(16.8) | 12.70(12.8) | |
| 55 | 114–115 | 48.39(48.0) | 6.12(6.00) | 13.90(14.0) | 16.29(16.0) | |
| 56 | 95–98 | 55.00(54.5) | 7.13(7.12) | 14.35(14.2) | 16.40(16.2) | |
| 57 | 189–190 | 52.95(52.8) | 4.09(4.03) | 11.09(11.2) | 12.86(12.8) | |
| 58 | 168–170 | 46.26(46.4) | 3.22(3.19) | 9.74(9.84) | 11.39(11.3) | 12.49(12.4) |
| 59 | 196–199 | 41.42(41.4) | 2.98(2.53) | 8.78(8.77) | 9.72(10.0) | 22.22(22.0) |
| 60 | 95(0.5mm)* | 50.12(51.2) | 5.41(4.9) | 9.87(9.9) | 22.50(22.8) | |
| 61 | 110(0.2mm)* | 50.14(51.7) | 3.56(3.6) | 10.27(10.1) | 22.90(23.0) | |
| 62 | 56–58 | 47.41(47.2) | 4.18(3.93) | 10.99(11.1) | 25.15(25.3) | |
| 63 | 84(0.02mm)* | 17.80(37.2) | 2.69(2.48) | 7.85(8.65) | 20.59(19.9) | 21.95(20.1) |
| 64 | 80–9 | 41.14(41.1) | 5.42(5.5) | 9.70(9.60) | 22.07(21.9) | |
| 65 | 156(dec) | 34.11(34.4) | 3.85(3.82) | 6.59(6.68) | 14.97(15.3) | 16.98(16.9) |
| 66 | 150(0.01mm)* | 52.50(52.4) | 6.53(6.55) | 6.05(6.11) | 14.00(14.0) | |
| 67 | 91–92 | 51.07(51.0) | 5.77(5.69) | 13.25(13.2) | 5.12(15.2) | |
| 68 | 130–133 | 40.45(42.2) | 3.56(3.53) | 11.75(12.3) | 27.38(28.6) | |
| 69 | 91–93 | 25.93(26.1) | 1.17(1.90) | 6.10(6.05) | 13.60(13.9) | 48.8(46.4) |
| 70 | 104–106 | 22.99(22.6) | 2.76(2.85) | 4.28(4.38) | 10.39(10.1) | |
| 71 | 100(0.02mm)* | 36.63(36.7) | 3.83(3.67) | 8.48(8.56) | 19.51(19.6) | 21.36(21.7) |
| 72 | 132–35 | 29.77(30.0) | 3.49(3.50) | 6.72(7.00) | 16.03(16.0) | 35.14(35.5) |
| 73 | 45–48 | 40.07(40.6) | 4.70(4.51) | 7.72(7.83) | 17.82(18.0) | 21.11(20.0) |
| 74 | 65–8 | 50.88(51.0) | 4.78(4.99) | 9.93(9.92) | 22.92(22.7) | |
| 75 | | 55.19(55.1) | 4.23(4.21) | 5.65(5.84) | 13.35(13.4) | 14.70(14.8) |
| 76 | 102(0.25 | 58.18(58.4) | 7.62(8.11) | 7.59(7.57) | 17.02(17.3) | |

TABLE II-continued

| Example No. | Melting Point in °C. | ANALYSIS[1] | | | | |
|---|---|---|---|---|---|---|
| | | C | H | N | S | Cl or Br |
| | mm)* | | | | | |
| 77 | | 60.53(60.3) | 8.54(8.59) | 7.07(7.02) | 16.10(16.1) | |
| 78 | 118–19 | 56.84(56.8) | 6.59(6.51) | 8.32(8.28) | 18.82(18.9) | |
| 79 | 142–44 | 51.02(51.1) | 2.59(2.86) | 6.42(6.63) | 14.88(15.2) | 16.55(16.8) |
| 80 | 155–57 | 44.20(43.9) | 1.70(2.05) | 5.52(5.69) | 12.60(13.0) | |
| 81 | 130–34 | 43.70(43.9) | 2.16(2.05) | 5.60(5.69) | 12.69(13.0) | |
| 82 | 145–47 | 43.71(43.9) | 2.08(2.05) | 5.58(5.69) | 12.85(13.0) | |
| 83 | 119–22 | 51.26(51.1) | 3.00(2.86) | 6.55(6.63) | 14.98(15.2) | |
| 84 | 19–2 | 61.31(61.1) | 4.03(3.98) | 7.86(7.90) | 17.70(18.0) | |
| 85 | 90–1 | 51.06(51.1) | 2.82(2.86) | 6.55(6.63) | 14.82(15.2) | |
| 86 | 118(0.01mm)* | 56.09(56.14) | 7.86(7.60) | 8.14(8.19) | 18.40(18.7) | |
| 87 | 84(0.15mm)* | 50.46(50.3) | 6.14(6.33) | | | |
| 88 | 114–15 | 41.18(41.4) | 4.91(4.83) | 9.54(9.65) | 21.80(21.2) | |
| 89 | | 21.01(20.8) | 2.69(2.42) | 4.80(4.84) | 11.31(11.0) | Br. 55.51(55.4) |
| 90 | 90–91 | 22.17(22.5) | 1.35(1.12) | 5.05(5.24) | 11.91(12.0) | 52.15(53.0) |
| 91 | 129–130 | 31.7(32.3) | 2.87(2.68) | 9.18(9.36) | 21.4(20.8) | 22.3(23.7) |
| 92 | 82–85 | 42.2(45.6) | 5.34(6.33) | 14.63(17.8) | 21.3(20.2) | |
| 93 | | 46.92(46.8) | 6.36(6.03) | 4.53(4.96) | 10.52(11.3) | 24.58(25.2) |
| 94 | | 53.09(53.4) | 7.75(7.33) | | 11.75(12.9) | 11.74(14.3) |
| 95 | 42–5 | 45.57(45.3) | 6.33(6.18) | 4.44(4.79) | 10.24(.0.9) | Br. 25.20(27.3) |
| 96 | 194–96 | 37.35(37.2) | 1.60(1.73) | 4.58(4.82) | 10.98(11.0) | Br. 27.99(27.5) |
| 97 | 150–53(dec) | 35.83(35.6) | 4.27(4.27) | 6.00(5.93) | 13.28(13.56) | Br. 33.91(33.9) |
| 98 | 117–118 | 24.37(24.2) | 1.90(1.61) | 6.01(5.64) | 12.58(12.9) | 42.25(42.8) |
| 99 | | 20.11(20.0) | 1.60(1.47) | 5.83(5.83) | 11.35(13.3) | Br. 48.7(50.0) |
| 100 | 115–17 | 41.42(40.9) | 1.71(2.00) | 4.70(4.70) | 11.13(10.8) | 36.00(36.1) |
| 101 | 145–47 | 51.14(51.3) | 4.51(4.66) | 5.52(5.44) | 12.08(12.4) | 13.66(13.8) |
| 102 | 84.5(0.2mm)* | 53.43(53.5) | 7.13(7.05) | 8.67(8.90) | 19.42(20.4) | |
| 103 | 75–8(.09mm)* | 50.94(53.5) | 6.71(7.05) | 8.42(8.90) | 19.15(20.4) | |

[1]The number parenthesized represents the theoretical value, as calculated, using the empirical formula of each compound.
*Boiling point in °C.
**Analysis for bromine.
[a]Neutralization equivalent.

The novel isothiazolones and salts of this invention are biocidally active compounds, and as such, are suitable for the control of living organisms and particularly microorganisms. For this reason, they are especially effective bactericidal, algaecidal, fungicidal, slimicidal, and pesticidal agents. Furthermore, these novel compounds possess the unexpected property of being resistant to inhibition by common additives or contaminants, such as lecithin, normal horse serum, alkylbenzene sulfonates, water-soluble lanolin, sodium chromate, sodium nitrite, glycerol, propylene glycol and the like.

It was also determined that other isothiazolones, namely, 2-methyl-3-isothiazolone and 2-ethyl-3-isothiazolone are likewise effective for the control of living organisms. These compounds were described by Leonard and Crow in the *Journal of Organic Chemistry* article previously cited. However, Leonard and Crow did not attribute any biocidal properties to the compounds. The use of these isothiazolones as biocides was unknown prior to the present invention.

Antibacterial and fungicidal activity were evaluated by the Serial Dilution Test (Broth Titer Test) wherein a series of broths containing varying dilutions of a test compound and an organism are halved starting with 1:1000. The values obtained, which are also shown in Table III, represent the maximum dilution at which the compound under evaluation renders complete control of the organism. *Staphylococcus aureus* (S. aureus) and *Escherichia coli* (E. coli) were the bacterial organisms employed in this test, and the fungi employed were *Aspergillus niger* (A. niger), *Rhizopus Stelonifer* (Rhiz.), and *Rhodotepula* sp. (Rode).

The 3-isothiazolones of the invention are also effective as algaecides. The algaecidal activity of the 3-isothiazolones was determined by the Fitzgerald Test (Applied Microbiology, 7, 205–211, No. 4, 1959). Table IV shows the parts per million of the 3-isothiazolone under evaluation necessary for complete control of the organism. *Chlorella pyrenoidosa* (Chlorella) and "Black" algae (Oscilatoria sp.) were the algae employed in this test.

TABLE III

| | MICROBIOLOGICAL ACTIVITY | | | |
|---|---|---|---|---|
| | FUNGISTATIC EVALUATION | | BACTERIOSTATIC EVALUATION | |
| Example No. | A. niger | Rhiz. (Rhodo.*) | S. aureus | E. coli |
| 1 | 1:16,000 | 1:32,000 | 1:8,000 | 1:32,000 |
| 2 | 1:8,000 | 1:8,000 | 1:4,000 | 1:8,000 |
| 3 | 1:16,000 | 1:125,000 | 1:8,000 | 1:32,000 |
| 4 | 1:8,000 | 1:64,000 | 1:32,000 | 1:8,000 |
| 5 | 1:16,000 | 1:8,000 | 1:8,000 | 1:1,000 |
| 6 | 1:4,000 | 1:64,000 | 1:32,000 | 1:64,000 |
| 7 | 1:125,000 | 1:500,000 | 1:128,000 | 1:256,000 |
| 8 | 1:32,000 | 1:125,000 | 1:64,000 | 1:64,000 |
| 9 | 1:16,000 | 1:16,000 | 1:32,000 | 1:64,000 |
| 10 | 1:2,000 | 1:4,000 | 1:2,000 | 1:4,000 |
| 11 | — | — | 1:256,000 | 1:1,000 |
| 12 | — | 1:8,000 | 1:512,000 | 1:2,000 |
| 13 | 1:16,000 | 1:250,000 | 1:128,000 | 1:64,000 |

TABLE III-continued
MICROBIOLOGICAL ACTIVITY

| | FUNGISTATIC EVALUATION | | BACTERIOSTATIC EVALUATION | |
|---|---|---|---|---|
| Example No. | A. niger | Rhiz. (Rhodo.*) | S. aureus | E. coli |
| 14 | 1:32,000 | >1:64,000 | 1:128,000 | 1:64,000 |
| 15 | 1:4,000 | 1:16,000 | — | — |
| 16 | 1:16,000 | 1:32,000 | 1:8,000 | 1:32,000 |
| 17 | — | — | 1:8,000 | 1:4,000 |
| 18 | 1:8,000 | 1:16,000* | 1:32,000 | 1:8,000 |
| 20 | 1:4,000 | 1:8,000* | | |
| 21 | 1:64,000 | 1:64,00* | 1:32,000 | 1:32,000 |
| 22 | 1:4,000 | 1:32,000* | 1:32,000 | 1:32,000 |
| 23 | 1:16,000 | 1:250,000 | 1:1,000,000 | 1:1,000 |
| 24 | 1:2,000 | 1:8,000 | 1:1,000 | <1:1,000 |
| 25 | 1:4,000 | 1:250,000 | 1:64,000 | 1:16,000 |
| 26 | 1:4,000 | 1:64,000 | 1:64,000 | 1:16,000 |
| 27 | 1:4,000 | 1:64,000 | 1:256,000 | 1:4,000 |
| 28 | 1:8,000 | 1:16,000 | 1:256,000 | 1:16,000 |
| 29 | 1:4,000 | 1:32,000 | 1:16,000 | 1:8,000 |
| 30 | 1:8,000 | 1:64,000 | 1:32,000 | 1:8,000 |
| 31 | 1:,32000 | 1:64,000 | 1:64,000 | 1:2,000 |
| 32 | 1:8,000 | 1:125,000 | 1:16,000 | 1:8,000 |
| 33 | 1:64,000 | 1:250,000 | 1:64,000 | 1:64,000 |
| 34 | 1:8,000 | 1:32,000 | 1:32,000 | 1:8,000 |
| 35 | 1:259,000 | 1:500,000 | 1:2,000,000 | 1:16,000 |
| 36 | 1:125,000 | 1:250,000 | 1:128,000 | 1:8,000 |
| 37 | 1:4,000 | 1:16,000 | 1:8,000 | <1:1,000 |
| 38 | 1:4,000 | 1:8,000 | 1:8,000 | <1:1,000 |
| 39 | 1:125,000 | 1:500,000 | 1:512,000 | 1:8,000 |
| 40 | 1:64,000 | 1:500,000 | 1:8,000 | 1:16,000 |
| 41 | — | — | 1:16,000 | 1:32,000 |
| 42 | — | — | 1:8,000 | 1:16,000 |
| 43 | 1:2,000 | 1:2,000 | 1:32,000 | 1:32,000 |
| 44 | 1:2,000 | 1:4,000 | 1:16,000 | 1:32,000 |
| 45 | 1:2,000 | 1:4,000 | 1:16,000 | 1:32,000 |
| 46 | <1:2,000 | 1:2,000 | 1:16,000 | 1:32,000 |
| 48 | 1:4,000 | 1:8,000 | 1:8,000 | 1:32,000 |
| 49 | 1:32,000 | 1:125,000 | 1:32,000 | 1:1,000 |
| 50 | 1:8,000 | 1:32,000 | 1:32,000 | 1:8,000 |
| 51 | 1:1,000 | 1:2,000 | 1:16,000 | 1:16,000 |
| 52 | 1:16,000 | 1:32,000 | 1:8,000 | 1:8,000 |
| 53 | 1:16,000 | 1:16,000 | 1:8,000 | 1:8,000 |
| 54 | 1:16,000 | 1:16,000 | 1:8,000 | 1:8,000 |
| 55 | 1:8,000 | 1:16,000 | 1:8,000 | 1:16,000 |
| 56 | 1:16,000 | 1:32,000 | 1:8,000 | 1:16,000 |
| 57 | 1:8,000 | 1:8,000 | 1:8,000 | 1:8,000 |
| 58 | 1:8,000 | 1:16,000 | 1:4,000 | 1:2,000 |
| 59 | 1:4,000 | 1:16,000 | 1:512,000 | 1:1,000 |
| 60 | 1:8,000 | 1:32,000 | 1:16,000 | 1:16,000 |
| 61 | 1:4,000 | 1:32,000 | 1:32,000 | 1:32,000 |
| 62 | 1:8,000 | 1:64,000 | 1:125,000 | 1:125,000 |
| 63 | 1:125,000 | 1:125,000 | 1:125,000 | 1:250,000 |
| 64 | — | — | 1:32,000 | 1:32,000 |
| 65 | <1:2,000 | 1:2,000 | <1:1,000 | 1:1,000 |
| 66 | 1:8,000 | 1:16,000 | 1:32,000 | 1:8,000 |
| 67 | 1:8,000 | 1:16,000 | 1:8,000 | 1:16,000 |
| 68 | 1:4,000 | 1:8,000 | 1:32,000 | 1:16,000 |
| 69 | 1:4,000 | 1:8,000 | 1:2,000 | 1:4,000 |
| 70 | — | — | 1:16,000 | 1:16,000 |
| 71 | 1:8,000 | 1:16,000 | 1:64,000 | 1:64,000 |
| 72 | 1:4,000 | 1:8,000 | 1:32,000 | 1:32,000 |
| 73 | 1:8,000 | 1:16,000 | 1:32,000 | 1:16,000 |
| 74 | 1:4,000 | 1:8,000 | 1:32,000 | 1:32,000 |
| 75 | 1:16,000 | 1:250,000 | 1:64,000 | 1:1,000 |
| 76 | 1:64,000 | 1:125,000 | 1:32,000 | 1:8,000 |
| 77 | 1:250,000 | 1:250,000 | 1:64,000 | 1:8,000 |
| 78 | 1:16,000 | 1:32,000 | 1:16,000 | 1:32,000 |
| 79 | 1:2,000 | 1:16,000 | 1:64,000 | 1:8,000 |
| 80 | <1:2000 | 1:2,000 | 1:16,000 | 1:1,000 |
| 81 | 1:2,000 | 1:4,000 | 1:32,000 | 1:1,000 |
| 82 | 1:4,000 | 1:2,000 | 1:1,000 | 1:1,000 |
| 83 | 1:4,000 | 1:2,000 | 1:32,000 | 1:16,000 |
| 84 | 1:2,000 | 1:64,000 | 1:128,000 | 1:16,000 |
| 85 | 1:2,000 | 1:2,000 | 1:32,000 | 1:1,000 |
| 86 | 1:32,000 | 1:500,000 | 1:16,000 | 1:16,000 |
| 87 | 1:4,000 | 1:16,000 | — | — |
| 88 | 1:2,000 | 1:2,000 | 1:1,000 | 1:1,000 |
| 89 | 1:4,000 | 1:8,000 | 1:32,000 | 1:64,000 |
| 90 | 1:8,000 | 1:16,000 | 1:4,000 | 1:8,000 |
| 91 | 1:8,000 | 1:8,000 | 1:16,000 | 1:8,000 |
| 92 | 1:4,000 | 1:16,000 | 1:16,000 | 1:32,000 |
| 93 | 1:16,000 | — | 1:32,000 | 1:8,000 |

TABLE III-continued

MICROBIOLOGICAL ACTIVITY

| Example No. | FUNGISTATIC EVALUATION | | BACTERIOSTATIC EVALUATION | |
|---|---|---|---|---|
| | A. niger | Rhiz. (Rhodo.*) | S. aureus | E. coli |
| 94 | 1:2,000 | 1:2,000 | <1:1,000 | 1:1,000 |
| 95 | 1:125,000 | 1:64,000 | 1:256,000 | 1:16,000 |
| 96 | 1:4,000 | 1:4,000 | 1:32,000 | 1:2,000 |
| 97 | 1:8,000 | 1:32,000 | 1:32,000 | 1:8,000 |
| 98 | 1:8,000 | 1:16,000 | 1:4,000 | 1:16,000 |
| 99 | 1:8,000 | 1:16,000 | 1:8,000 | 1:16,000 |
| 100 | 1:8,000 | 1:32,000 | 1:256,000 | <1:1,000 |
| 101 | 1:4,000 | 1:16,000 | 1:16,000 | 1:4,000 |
| 102 | 1:8,000 | 1:16,000 | 1:4,000 | 1:8,000 |
| 104 | 1:125,000 | 1:250,000 | 1:250,000 | 1:64,000 |
| 105 | | 1:32,000[1] | 1:32,000[2] | |
| 106 | | 1:1,000,000[1] | 1:64,000[2] | |
| 2-methyl-3-isothiazolone | 1:4,000 | 1:8,000 | 1:16,000 | 1:32,000 |
| 2-ethyl-3-isothiazolone | 1:4,000 | 1:16,000 | 1:8,000 | 1:16,000 |

[1] Mixed culture - A. niger, Rhiz.
[2] Mixed culture - S. aureus E. coli.

TABLE IV

ALOAESTATIC ACTIVITY

| Example No. | Chlorella | Oscilatoria |
|---|---|---|
| 1 | 2 | 5 |
| 3 | 5 | 5 |
| 4 | 1 | 1 |
| 5 | 10 | — |
| 6 | 1 | 0.75 |
| 7 | 0.125 | 0.125 |
| 8 | 0.25 | 0.125 |
| 9 | 0.3 | 0.16 |
| 10 | 2 | — |
| 11 | 2 | 1 |
| 12 | 10 | 1 |
| 13 | 0.25 | 0.125 |
| 14 | 0.25 | 0.125 |
| 15 | 0.5 | <0.125 |
| 16 | 5 | 5 |
| 18 | 10 | 10 |
| 20 | 5 | — |
| 21 | 10 | 0.5 |
| 22 | 2 | 10 |
| 23 | 2 | <0.5 |
| 24 | 2 | <0.5 |
| 25 | 1 | 1 |
| 26 | 2 | 5 |
| 27 | 5 | 2 |
| 28 | 2 | 2 |
| 29 | 10 | 10 |
| 30 | 10 | 10 |
| 31 | 5 | 10 |
| 33 | 1 | 1 |
| 34 | — | 10 |
| 35 | 1 | 1 |
| 36 | 1,5 | 2,5 |
| 38 | 1 | 1 |
| 39 | 1 | 2 |
| 40 | 1 | 2 |
| 43 | 0.5 | 10 |
| 44 | — | 10 |
| 46 | — | 2 |
| 48 | — | 0.5 |
| 49 | 2.5 | 10 |
| 50 | 10 | 0.5 |
| 52 | 5 | 10 |
| 53 | 5 | 5 |
| 54 | 5 | 10 |
| 55 | 2 | 2 |
| 56 | 2 | 5 |
| 57 | 2 | <0.5 |
| 58 | 2 | <0.5 |
| 59 | 10 | <0.5 |
| 60 | 1.25 | 2.5 |
| 62 | 5 | 0.3 |
| 63 | <0.5 | <0.5 |
| 66 | — | 1 |
| 67 | 5 | — |
| 68 | — | <0.5 |
| 69 | 5 | <0.5 |
| 71 | 5 | 2 |
| 73 | 10 | 5 |
| 74 | 2.5 | 2.5 |
| 75 | 2.5 | 2.5 |
| 76 | 5 | 10 |
| 77 | 2 | 0.5 |
| 78 | 5 | 10 |
| 79 | 5 | <0.5 |
| 84 | 2 | 0.5 |
| 88 | — | 10 |
| 89 | — | 5 |
| 90 | 10 | 5 |
| 91 | 10 | — |
| 92 | 2 | 1 |
| 93 | 5 | 2 |
| 95 | 1 | 1 |
| 96 | 10 | 0.5 |
| 97 | 5 | 2 |
| 104 | 0.63 | 0.63 |

Further fungicidal activity on the part of the isothiazolones was demonstrated by their utilization in seed treatment applications. By seed treatment is meant the disseminating of a biocidally active material over a seed subject to the attack of microorganisms, and particularly fungi, in an amount which is effective to control such microorganisms without deleteriously effecting the seed. In most circumstances, the biocidally active material, in this case, the isothiazolones or compositions thereof will be applied to the surface area of the seeds to be treated. This may be accomplished by varying means common to the art, such as slurrying, soaking, dusting, spraying and the like.

The amount of isothiazolone required so as to be effective in a seed treatment application will vary depending upon conditions, such as the type of seed, the method of application, soil and atmospheric conditions and the like. Generally, an application in the range of about 0.25 to 20 ounces of active ingredient, namely, the isothiazolone per 100 pounds of seed will be effective to control any undesirable microorganisms and so provide protection to the seed. An applicatiion of active agent in the range of about 1.0 to 10 ounces per 100 pounds of seed is preferred.

An experimental technique was employed to demonstrate the effectiveness of these compounds for seed treatment. This involved slurrying two lots of 100 corn seeds each with the isothiazolone under evaluation at a level of 1 to 2 ounces per bushel of seed. For purposes of comparison, an untreated control was also included. After drying, the seeds were planted in a muck soil infested with Pythium and having a high moisture content. The corn seeds were maintained in this soil for a week at about 10° C. so as to permit infection. Upon completion of this period of time, the temperature was elevated and maintained at about 21° to 27° C. so as to permit germination of the non-infected seed. The number of seeds germinating were counted after emergence of the plant and such data is set forth in Table V.

TABLE V
SEED TREATMENT

| Test Compound | No. of Plants Germinating/200 Seeds |
|---|---|
| untreated | 10 |
| 2-t-butyl-3-isothiazolone | 100 |
| 2-n-hexyl-3-isothiazolone | 172 |
| 2-n-octyl-3-isothiazolone | 144 |
| 2-t-octyl-3-isothiazolone | 184 |
| 2-n-nonyl-3-isothiazolone | 164 |
| 2-n-decyl-3-isothiazolone | 153 |
| 2-methyl-5-chloro-3-isothiazolone | 150 |
| 2-methyl-4,5-dichloro-3-isothiazolone | 140 |
| 2-n-octyl-5-chloro-3-isothiazolone | 150 |
| 2-t-octyl-4-chloro-3-isothiazolone | 160 |
| 2-t-octyl-4-bromo-3-isothiazolone | 148 |
| 2-(2,4-dichlorobenzyl)-3-isothiazolone | 80 |
| 2-(2-ethylhexyl)-3-isothiazolone | 182 |
| 2-(1-phenylethyl)-3-isothiazolone | 176 |
| 2-(2-phenylethyl)-3-isothiazolone | 160 |
| 2-cyclohexyl-3-isothiazolone | 168 |
| 2-benzyl-3-isothiazolone | 136 |
| 2-hydroxymethyl-3-isothiazolone | 182 |

Evaluation of the isothiazolones with regard to pesticidal activity demonstrated their exceptional control of numerous nematodes, mites, insects, such as beetles and aphids, and the like. Some typical nematodes, insects and mites which were controlled when contacted with the compounds of this invention included the following: Northern root knot nematode (*Meloidogyae hapla*), Mexican bean beetle (*Epilachna varivesta*), black carpet beetle (*Attagenus piceus*), confused flour beetle (*Tribolium confusum*), granary weevil (*Sitophilus granarius*), two spotted mite (*Tetranychus urticae*), house fly (*Musca domestica*), Southern armyworm (*Prodenia eridania*), German cockroach (*Blattella germanica*), and green peach aphid (*Hyzus persicae*).

Generally, control of a living organism is achieved in accordance with this invention by contacting the organism with an isothiazolone in an amount which is effective to control said organism. Any of the techniques known in the art can be employed to disseminate the isothiazolones in a manner so as to achieve the desired contact with the organism to be controlled. Spraying and fumigating are typical of such techniques.

The compounds of this invention can be readily utilized as slimicides, algaecides, bactericides, and fungicides in any locus and particularly in aqueous media, such as, for example, water-cooling systems, swimming pools, paper pulp processes, aqueous polymer dispersions, water-based paints, and the like. In addition, those compounds and compositions containing them can function as, for example, fabric and leather preservatives, cosmetic preservatives, soap additives, sanitizing agents, such as in laundry soaps and detergents, and preservatives for metal working compounds, such as emulsifiable cutting oils, preservatives for fuels, fiber spin finish biocides, and the like.

In general, a locus subject to contamination by microorganisms can be protected in accordance with this invention by incorporating into the locus an isothiazolone or a salt of an isothiazolone in an amount which is effective to control said microorganisms. The term "contamination" is meant to include any attack by microorganisms which leads to a chemical or physical breakdown or disintegration of the locus as well as the proliferation of the microorganisms within the locus without an accompanying deleterious effect. The exact amount of isothiazolone required will, of course, vary with the medium being protected, the microorganisms being controlled, the particular isothiazolones or compositions containing the isothiazolones being employed and other factors. Typically, in a liquid medium, excellent control is obtained when the isothiazolones are incorporated in the range of 0.1 to 10,000 parts per million (ppm) or 0.00001 to 1% based on the weight of the medium. A range of 1 to 2000 ppm is preferred.

The term "control," as employed in the specification and claims of this application is to be construed as the effect of any means which adversely affects the existence or growth of any living organism or microorganism. This effect may comprise a complete killing action, eradication, arresting in growth, inhibition, reduction in number or any combination thereof.

Outstanding fungistatic activity is exhibited by the isothiazolones when they were employed as paint preservatives and paint fungistats. Microbial activity in water-based and oil-based paint emulsions is effectively inhibited when the isothiazolones are incorporated into the paint. The isothiazolones are also highly active mildewcides for paint films when incorporated in paint formulations.

The isothiazolones of this invention are especially useful as agricultural fungicides. As such, they are particularly valuable when formulated in a fungicidal composition. Such compositions normally comprise an agronomically acceptable carrier and an isothiazolone or mixture of isothiazolones as the active agent. Where necessary or desirable, surfactants or other additives may be incorporated to give uniformly formulated mixtures. By "agronomically acceptable carrier" is meant any substance which can be utilized to dissolve, dispense or diffuse the chemical incorporated therein without impairing the effectiveness of the toxic agent and which does no permanent damage to such environment as soil, equipment and agronomic crops.

For use as pesticides, the compounds of this invention are usually taken up in an agronomically acceptable carrier or formulated so as to render them suitable for subsequent disemination. For example, the isothiazolones can be formulated as wettable powders, emulsion concentrates, dusts, granular formulations, aerosols or flowable emulsifiable concentrates. In such formulations, the isothiazolones are extended with a liquid or solid carrier and, when desired, suitable surfactants are likewise incorporated.

Compounds of this invention can be dissolved in a water-miscible liquid, such as ethanol, isopropanol, acetone, and the like. Such solutions are easily extended with water.

The isothiazolones can be taken up on or mixed with a finely particled solid carrier, as for example, clays, inorganic silicates, carbonates, and silicas. Organic carriers can also be employed. Dust concentrates are commonly made wherein isothiazolones are present in the range of 20 to 80%. For ultimate applications, these concentrates are normally extended with additional solid from about 1 to 20%.

Wettable powder formulations are made by incorporating the compounds of this invention in an inert, finely divided solid carrier along with a surfactant which may be one or more emulsifying, wetting, dispersing or spreading agents or blend of these. The isothiazolones are usually present in the range of 10 to 80% by weight and the surfactants in from 0.5 to 10% by weight. Commonly used emulsifying and wetting agents include polyoxyethylated derivatives of alkylphenols, fatty alcohols, fatty acids, and alkylamines, alkylarene sulfonates and dialkyl sulfosuccinates. Spreading agents include such materials as glycerol mannitan laurate and a condensate of polyglycerol and oleic acid modified with phthalic anhydride. Dispersing agents include such materials as the sodium salt of the copolymer of maleic anhydride and an olefin such as diisobutylene, sodium lignin sulfonate and sodium formaldehydenaphthalene sulfonates.

One convenient method for preparing a solid formulation is to impregnate the isothiazolone toxicant onto the solid carrier by means of a volatile solvent, such as acetone. In this manner adjuvants, such as activators, adhesives, plant nutrients, synergists and various surfactants, can also be incorporated.

Emulsifiable concentrate formulations can be prepared by dissolving the isothiazolones of this invention in an agronomically acceptable organic solvent and adding a solvent-soluble emulsifying agent. Suitable solvents are usually water-immiscible and may be found in the hydrocarbon, chlorinated hydrocarbon, ketone, ester, alcohol and amide classes of organic solvents. Mixtures of solvents are commonly employed. The surfactants useful as emulsifying agents may constitute about 0.5 to 10% by weight of the emulsifiable concentrate and may be anionic, cationic or non-ionic in character. Anionic surfactants include alcohol sulfates or sulfonates, alkylarene sulfonates and sulfosuccinates. Cationic surfactants include fatty acid alkylamine salts and fatty acid alkyl quaternaries. Non-ionic emulsifying agents include alkylene oxide adducts of alkylphenols, fatty alcohols, mercaptans and fatty acids. The concentration of the active ingredients may vary from 10 to 80%, preferably in the range of 25 to 50%.

For use as phytopathogenic agents, these compounds should be applied in an effective amount sufficient to exert the desired biocidal activity by techniques well known in the art. Usually, this will involve the application of the isothiazolones to the locus to be protected in an effective amount when incorporated in an agronomically acceptable carrier. However, in certain situations it may be desirable and advantageous to apply the compounds directly onto the locus to be protected without the benefit of any substantial amount of carrier. This is a particularly effective method when the physical nature of the isothiazolone is such as to permit what is known as "low-volume" application, that is, when the compounds are in liquid form or substantially soluble in higher boiling solvents.

The application rate will, of course, vary depending upon the purpose for such application, the isothiazolones being utilized, the frequency of dissemination and the like.

For use as agricultural bactericides, fungicides, nematocides, and insecticides, dilute sprays can be applied at concentrations of 0.05 to 20 pounds of the active isothiazolone ingredient per 100 gallons of spray. They are usually applied at 0.1 to 10 pounds per 100 gallons and preferably at 0.125 to 5 pounds per 100 gallons. In more concentrated sprays, the active ingredient is increased by a factor of 2 to 12. With dilute sprays, applications are usually made to the plants until run-off is achieved, whereas with more concentrated or low-volume sprays the materials are applied as mists.

The compounds of this invention may be utilized as the sole biocidal agents or they may be employed in conjunction with other fungicides, bactericides, algaecides, slimicides, insecticides, miticides, or with other comparable pesticides.

In field tests, the isothiazolones described above were effective in controlling fungi which cause broccoli downy mildew (*Peronospora parasitica*), bean powdery mildew (*Erysiphe polygoni*), wheat powdery mildew (*Erysiphe graminis*), rice blast (*Piricularia oryzae*), and tomato blights (*Phytothora infestans*) and (*Alternaria solani*).

The following examples A through E illustrate several specific embodiments of the many uses of the isothiazolones of the invention.

EXAMPLE A

Preservatives for Cutting Oils

Both natural and synthetic cutting oils, that is, oils which are mixed with water and used as coolants and lubricants in, for example, lathe and other metal-working operations, are extremely susceptible to microbial attack when formulated for use. This microbial attack leads to the production of odor and to the eventual breakdown of the oil formulation. The isothiazolones of the invention are extremely useful in controlling microbial build-up, thus preventing this deleterious microbial attack, when incorporated in an emulsion or other diluted use formulation, either before or after the emulsification, at a level of about 10 to 10,000 parts per million of the use formulation. The preferred range of incorporation is about 20 to about 2000 parts per million in the final emulsion.

In order to evaluate the isothiazolones as preservatives, samples of contaminated cutting oil from actual use operations were obtained. These contaminated samples were used to inoculate uncontaminated cutting oil formulations to which an isothiazolone had been added. After one month, the formulation was examined to determine whether the isothiazolone was effective in controlling microbial attack, and, if so, the formulation was recontaminated. This examination and recontamination procedure was followed for a period of six months.

Three formulations were employed in testing the isothiazolones. In the first formulation, the isothiazolone was added to a 1:60 oil-water emulsion of an emulsifiable cutting oil containing petroleum oil and special emulsifiers (commercially available as Gulf's Gulfcut Soluble Oil). The inoculum for the first formulation was a naturally contaminated oil emulsion. The results of this test are summarized in Table VI, which lists the isothiazolones tested and the minimum concentration (in parts per million) of the isothiazolone which is effective in controlling microbial attack for six months.

TABLE VI

Emulsifiable Cutting Oil Preservatives

| Isothiazolone | Min. Effective Conc. (ppm) |
| --- | --- |
| 2-n-butyl-3-isothiazolone | 100–250 |
| 2-n-hexyl-3-isothiazolone | 20–30 |
| 2-n-octyl-3-isothiazolone | 20–30 |
| 5-chloro-2-methyl-3-isothiazolone | $\leq 100$ |
| 2-benzyl-3-isothiazolone | 20–30 |
| 2-phenyl-3-isothiazolone | 50–100 |
| 2-cyclohexyl-3-isothiazolone | 500 |
| 2-(4-chlorobenzyl)-3-isothiazolone | 50 |
| 2-(3,4-dichlorobenzyl)-3-isothiazolone | 500 |
| 2-methyl-4,5-dichloro-3-isothiazolone | 40 |

In the second formulation, the isothiazolone was added to a 1:40 oil-water dilution of a synthetic cutting oil made up of triethanolamine, sulfonated red oils, sodium nitrate, an anionic free acid of a complex organic phosphate ester, and water (commercially available as H. Miller's Hamikleer No. 1591 Soluble Oil). The inoculum for the second formulation was a naturally contaminated soluble oil emulsion to which was added *Pseudomonas oleoverans* one of the most troublesome contaminants of cutting fluid emulsions. The results of this test are summarized in Table VII, which lists the isothiazolones tested and the minimum concentration (in parts per million) of the isothiazolone which is effective in controlling microbial attack for two months. In the third formulation, the isothiazolone was added at 0.5% to the Hamikleer No. 1591 Soluble Oil prior to dilution with water. The inoculum was a naturally contaminated soluble oil to which *Pseudomonas oleoverans* was added. The oil was then diluted to a 1:40 oil-water use formulation, in which the concentration of the isothiazolone was 125 ppm. After one month, the formulation was examined to determine the number of bacteria surviving per milliliter of the emulsion. The results of this test are summarized in Table VII.

TABLE VII

Synthetic Cutting Oil Preservatives

| Isothiazolone | Min. Effect. Conc. (ppm) | Bacteria/ml (after 1 mo) |
| --- | --- | --- |
| 2-n-butyl-3-isothiazolone | $\leq 25$ | 0 |
| 2-n-hexyl-3-isothiazolone | 100–250 | 0 |
| 2-benzyl-3-isothiazolone | 50 | 0 |
| None | | 7,600,00 |

By way of comparison, it was determined that 500 ppm of ethylhexyldimethylalkylammonium cyclohexylsulfamate, a commercial cutting oil preservative, was ineffective in controlling bacterial attack in the Hamikleer cutting oil formulation.

The data from the above tests indicates the great effectiveness of the isothiazolones of the invention as preservatives, when incorporated in cutting oil formulations.

EXAMPLE B

Control of Algae, Bacteria, Fungi, and Slime in Cooling Towers

A constantly recurring problem in water-cooling systems is the out-of-control growth of algae, bacteria, and fungi, and the associated formation of slime. The isothiazolones of the invention are quite effective in controlling algae, bacteria, fungi, and slime formation in water-cooling systems, and especially in water-cooling towers. When used as a cooling tower microbicide, the isothiazolone will generally be added at a concentration of about ½ to 1000 parts per million. The preferred concentration range of the isothiazolone is about 1 to 250 parts per million.

The following test was employed to evaluate the isothiazolones as cooling tower microbicides.

A series of laboratory cooling towers, operated concurrently, was used for the evaluation study. The cooling tower liquid was an inorganic salts medium, designed to promote algal development. Approximately 8 liters of this liquid were held in the reservoir, at 35° C., and continuously recirculated over pine wood slats at a rate of 2.3 liters per minute. A similar, but more dilute medium was pumped continuously into each cooling tower reservoir at a rate of 150 ml./hr. This was sufficient to replenish the volume lost in evaporation and to provide the system with a bleed-off of approximately 8 liters in 3 days. A constant volume was maintained in the reservoir by use of an over-flow drain.

The cooling towers were heavily inoculated at the beginning of the study and twice per week thereafter with microorganisms (algae, bacteria, and fungi) obtained from a large commercial cooling tower. If necessary, the first two weeks of operation were used to establish an adequate population of microorganisms on the surfaces and in the reservoir, and, in addition, to determine volume losses due to evaporation. When starting with a fouled tower, treatment was initiated by the addition of the isothiazolone at double the intended dose. When starting with a clean tower, treatment was initiated by the addition of the isothiazolone at the maintenance dose. The isothiazolone was then added periodically, usually once a week, to the diluting systems to restore the concentration levels to the intended maintenance dose. Four factors were considered in evaluating the effectiveness of the isothiazolenes as cooling-tower microbicides—control of algae and control of non-algal slime as reflected in the appearance of the tower, and general control of bacteria and fungi in the water itself. Three isothiazolones were tested by the above procedure and found to be effective at the indicated minimum concentration in parts per million. These isothiazolones were 2-n-hexyl-3-isothiazolone, at 5 ppm, 2-n-octyl-3-isothiazolone, at 5 ppm, and 5-chloro-2-methyl-3-isothiazolone, at 2.5 ppm. The hydrochloride salt of 5 chloro-2-methyl-3-isothiazolone was also found to be effective.

In a supplementary test, isothiazolones were evaluated in controlling bacterial and fungal populations in water samples taken from actual commercial cooling towers. The water sample from the cooling tower was employed as the diluent in preparing the dosage series of the isothiazolone being tested, and each diluted sample was examined for viable microorganisms 48 hours after the dilution. The minimum dose at which a zero plate count was obtained was considered to be the minimum inhibitory concentration for each isothiazolone tested. Under actual use conditions, a certain bacterial count might be tolerated, however, if the microbicide tested can keep the count from increasing and thus avoid slime formation. The results of this test are summarized in Table VIII, which lists the isothiazolones tested, and the average minimum inhibitory concentration (in parts per million) for each isothiazolone.

TABLE VIII
Water Treatment Microbicides

| Isothiazolone | Min. Inhibitory Conc. (ppm) |
| --- | --- |
| 2-t-octyl-3-isothiazolone | 500 |
| 2-n-docyl-3-isothiazolone | 37 |
| 2-benzyl-3-isothiazolone | 188 |
| 4,5-dichloro-2-methyl-3-isothiazolone | 188 |

The above tests demonstrate the effectiveness of the isothiazolones of the invention as water-cooling system microbicides.

EXAMPLE C
Paint Film Mildewcides

Paint films from water-based and oil-based paints are quite susceptible to mildewing, especially when applied on exterior surfaces. Presently, various mercury compounds are generally used as paint mildewcides. However, those mercury compounds have several disadvantages, including their susceptibility to sulfide staining and their toxicity. The isothiazolones of the invention are quite effective as paint mildewcides without the disadvantages of the mercurial mildewcides, and often with better performance than the mercury compounds. The concentration of isothiazolone which is added to the paint can vary over a wide range depending on such factors as the type of paint involved, the locality of application, and the type of surface on which the paint is applied. Generally, about 1/10 lb to 20 lb. of isothiazolone per 100 gallons of paint will be effective. The preferred range of incorporation is about ½ lb. to 12 lb. isothiazolone per 100 gallons of paint.

In order to evaluate isothiazolones as paint mildewcides, wood sticks were painted with water-based paint formulations to which the isothiazolone being tested has been added. The paint films were allowed to dry for two days, treated with a test fungus (*Aspergillus niger* or *Aspergillus cryzac*) and after 7 to 10 days were examined for evidence of mildew formation. The results of these tests are summarized in Table IX, which lists the isothiazolones tested and the minimum concentration (in pounds of isothiazolone per 100 gallons of paint) of isothiazolone which inhibits the growth of the fungus.

TABLE IX
Paint Film Mildewcides

| Isothiazolone | Min. Mildew Protection Level (lb./100 gal.) |
| --- | --- |
| 2-n-butyl-3-isothiazolone | 0.5–2 |
| 2-n-hexyl-3-isothiazolone | 0.5 |
| 2-n-octyl-3-isothiazolone | 0.25–2 |
| 2-n-decyl-3-isothiazolone | 4 |
| 2-benzyl-3-isothiazolone | 10 |
| 5-chloro-2-methyl-3-isothiazolone | <0.25 |
| 2-cyclohexyl-3-isothiazolone | 0.5–1 |
| 4,5-dichloro-2-methyl-3-isothiazolone | 0.25 |
| 5-chloro-2-benzyl-3-isothiazolone | <0.25 |

In addition to the above test, 2-n-butyl-3-isothiazolone, 2-n-hexyl-3-isothiazolone, 2-n-octyl-3-isothiazolone, and 2-n-decyl-3-isothiazolone were found to be equally effective when tested in paint films from oil-based paints. Panels painted with paints containing 2-n-butyl-3-isothiazolone, 2-n-hexyl-3-isothiazolone, and 2-n-octyl-3-isothiazolone were field tested and showed good to excellent resistance to mildew attack after at least six months of outdoor exposure.

The above tests and data demonstrate the excellent qualities of the isothiazolones when used as paint film mildewcides.

EXAMPLE D
Preservatives for Vinyl or Acrylic Emulsion Polymer Dispersions On storage, aqueous dispersions of vinyl or acrylic emulsion polymers, such as those used in making water-based paints, may be subject to a buildup of microorganisms which may lead to the production of odor or discoloration in the dispersion or to actual physical or chemical breakdown of the polymer.

Examples of such polymer dispersions include polyvinyl acetate; polyisobutylene; polystyrene; polymers of dienes, such as of isoprene, chloroprene, butadiene, including copolymers of butadiene with styrene, acrylonitrile or mixtures thereof; copolymers of (a) a soft acrylate, such as a ($C_1$–$C_8$) alkyl acrylate (especially methyl acrylate, ethyl acrylate, butyl acrylate, 2-ethylhexyl acrylate or mixtures thereof), with (b) at least one hard comonomer, such as methyl methacrylate, acrylonitrile, styrene, vinyltoluene, vinyl acetate, and vinyl chloride, and (c) about 0.5 to 8% by weight of an $\alpha,\beta$-monoethylenically unsaturated acid, such as acrylic, methacrylic, crotonic, or itaconic acid such as those described in Conn et al U.S. Pat. No. 2,795,564, June 11, 1957; and blends of any of these polymer dispersions with each other or with similar polymers containing a polar group, such as any of the blends mentioned in Scott U.S. Pat. No. 3,356,627, Dec. 5, 1967.

The isothiazolones of the invention are extremely effective in controlling build-up of microorganisms in such aqueous polymer dispersions and in water-base paints made from them thus preventing deleterious contamination of the dispersion or paint. An advantage of using the isothiazolones as preservatives is that in proper concentration they will also function as mildewcides after the polymer dispersion or paint has been used to make a coating or film. When employed as preservatives, the isothiazolones are usually incorporated in the polymer dispersion in a concentration range of about ½ to 10,000 parts per million. The preferred concentration rante is about 1 to 2000 parts per million.

In order to evaluate the isothiazolones as preservatives for polymer dispersions, various samples of different types of emulsion polymer dispersions, to which an isothiazolone had been added, were contaminated with an inoculum consisting of naturally contaminated dispersion of the same type or with a culture of organisms isolated from naturally contaminated dispersions of the same type. For a period of six months, the samples were examined monthly for microbial contamination and then reinoculated with fresh inculum.

The isothiazolones were evaluated as preservatives in several different types of commercially available acrylic polymer dispersions, of the type described in the Conn et al and Scott U.S. patents mentioned above. Among the isothiazolones which were tested in one or more of such acrylic polymer dispersions and found to give control of microbial activity at a concentration of less than 1000 ppm in the dispersion are 2-n-butyl-3-isothiazolone, 2-n-hexyl-3-isothiazolone, 2-benzyl-3-isothiazolone, and 5-chloro-2-methyl-3-isothiazolone. In some of the dispersions, these isothiazolones resulted in control of microbial activity at a concentration of less than 100 ppm.

EXAMPLE E

Laundry Sanitizers

In order to sanitize the wash water, to kill bacteria in dirty clothes, and to prevent transfer of bacteria from dirty to clean clothes, it is desirable to incorporate a sanitizing ingredient into laundry soaps and detergents. The isothiazolones of the invention have been found to be useful as laundry sanitizing agents. A wide concentration range can be employed in formulating detergents or soaps with the isothiazolones of the invention as sanitizing agents. Generally, about 0.01 to 10% of the isothiazolone will be added to the soap or detergent, and the preferred range is about 0.05 to 5%. The isothiazolone can also be added directly to the wash water, generally at a concentration of about ½ to 1000 parts per million.

In order to evaluate the isothiazolones of the invention as laundry sanitizing agents, several tests were employed. Initially, a time survival test was undertaken, employing the following procedure:

One milliliter of inoculum (the growth from one 24 hour slant suspended in 20 ml. of phosphate buffer, using *Fscherichia coli* and *Staphylococcus aureus* as the test organisms) is added to 99 ml. of test solution (a 0.25% solution of a synthetic laundry detergent formulation containing the desired concentration of the compound under test) and the flask agitated to insure thorough mixing. Exactly 5 minutes, 10 minutes and 15 minutes following inoculation, one ml. aliquots of the inoculated test solution are removed from the test flask and placed in sterile 9 ml. neutralizing blanks. The blanks are agitated vigorously to assure complete homogenity and the resulting solution is then plated at 0, $10^2$, $10^3$ and $10^4$ dilution with Tryptone-Glucose-Extract Agar containing additional neutralizer. All of the preceding steps were run at 25° C. The plates are incubated at 37° C. for 48 hours and then observed for total number of colonies. The results of the colony counts are recorded as surviving bacteria per ml. of original test solution, taking into consideration the dilution factor of the neutralizing blank and the dilution represented by the countable plate. The results of the time survival to test are summarized in Table X.

TABLE X

| | Time Survival Test | | |
|---|---|---|---|
| | Min. Effective Conc. (ppm) | | |
| Isothiazolone | 5 min. exp. | 10 min exp. | 15 min. exp. |
| 2-n-octyl-3-isothiazolone | 75 | 50 | 10-25 |
| 2-n-decyl-3-isothiazolone | 75 | 25 | 10-25 |

The isothiazolones were then evaluated for fabric sanitization activity and for wash water sanitization effectiveness.

A series of tests under actual cold water home laundry conditions was conducted in an automatic washer using 12 gallons of cold water, a cold water rinse, and a medium load of 4 lbs. of turkish towels as an equivalent to a typical home laundry load. The detergent product used in the washer tests was a typical linear alkylate sulfonate (LAS) detergent formulation.

The operation schedule of the machine employed is as follows:

| Operation | Accumulated Time in Minutes | Time in Minutes For Each Operation |
|---|---|---|
| fills | 0-4 | 4 |
| washes | 4-18 | 14 |
| stops | 18-19 | 1 |
| empties | 19-20 | 1 |
| spins | 20-22 | 2 |
| fills | 22-26 | 4 |
| rinses | 26-28 | 2 |
| stops | 28-29 | 1 |
| empties | 29-30 | 1 |
| spins | 30-32 | 2 |

The detergent formulation was employed at a concentration in the wash water of 0.25%. The isothiazolone being tested was added to the wash water at a level of 50 ppm. The turkish bath towels used in the tests were pre-washed, dried and sterilized before use. Swatches of cotton Test Fabric 400 (2,3" swatches; 6, 1⅜" swatches; 4 or 8, 1⅞" diameter circular swatches) had been stapled to each of the towels in each of the total of 10 runs made in the washing machine.

In a typical run, 113.5 gms. of the detergent (0.25%) were added to 12 gallons of cold wash water (15°-17° C.) using a four pound turkish towel ballast. The isothiazolone was added by removing 450 ml. of wash water and replacing it with 450 ml. of anhydrous alcohol containing 2.271 grams compound. This gave a concentration of 50 ppm of the isothiazolone in the wash water. The swatch towel to be inoculated was not yet added. The machine was agitated for one minute. As a check for bacterial content before inoculation, one milliliter of solution was removed aseptically from the washer and placed into a sterile 9 ml. neutralizer blank containing 0.5% sodium thioglycollate solution. The swatch-containing towel was then inoculated with 4 ml. of a 24 hr. culture of S. aureus in AATCC Broth—3 ml. of inoculum were pipetted onto one of the 3" swatches and 1 ml. onto one of the 1⅜" swatches. After placing the inoculated towel in the washer, the machine was restarted and one milliliter aliquots of wash water were removed aseptically at various points during the wash and rinse cycles. Each 1 ml. aliquot was placed into a sterile 9 ml. neutralizer blank containing 0.5% sodium thioglycollate. These samples were then plated with Tryptone-Glucose-Extract Agar containing 0.025% sodium thioglycollate and incubated for 48 hrs. at 37° C. A count was also made on the S. aureus inoculum to determine how many organisms would be introduced per ml. of wash water.

The cotton swatches of Test Fabric-400 were removed aseptically from the towel. The 3" inoculum swatch as well as the other 3" swatch were each placed into 100 ml. of sterile 0.5% sodium thioglycollate solution, shaken vigorously for one minute and the elution was plated in duplicate in Tryptone-Glucose-Extract Agar containing 0.025% sodium thioglycollate.

The 1⅜" swatch as well as another 1⅜" swatch were placed in sterile Petri dishes and covered with Tryptone Glucose Extract Agar containing 0.05% sodium thioglycollate. All the plates were incubated for 48 hours at 37° C.

The remaining 1⅜" swatches as well as the circular swatches were placed in sterile Petri dishes and retained for testing by modified test methods AATCC 90-1965 T and AATCC 100-1965 T.

The procedure used in other runs was then the same as that above, while varying the inoculum and the isothiazolone tested.

The results of the wash water sanitization studies, the washed fabric swatch elutions, the plated washed fabric swatches and the residual activity of the washed fabric swatches will be found in Tables XI and XII.

Table XI summarizes the results of the evaluation of 2-n-decyl-3-isothiazolone and Table XII summarizes the results of the evaluation of 2-n-octyl-3-isothiazolone.

The isothiazolones were also tested to determine the antibacterial residual which they imparted to fabrics.

Desized Test Fabric-400 was treated with aqueous solutions of the various isothiazolones under evaluation according to the tentative AOAC Laboratory Treatment Method (Spindle Type). The actual treatment was carried out in an Atlas Launderometer for 5 minutes at 25° C. using a 1:10 fabric to treatment solution ratio.

Evaluation of the effectiveness of the antibacterial residuals imparted to the fabric was carried out by means of the tentative AOAC Modification of AATCC Methods 90-1965 T and 100-1965 T (Technical Manual of the American Association of Textile Chemists and Colorists, Volume 44, 1968, pages B-175 to B-178). AATCC Method 90-1965 T measures the "bacteriostatic" residual and AATCC Method 100-1965 T measures the "self-sanitizing" residual in the fabric.

The results of the evaluations are given in Table XIII. It will be noted that all three isothiazolones were able to impart a bacteriostatic residual against both S. aureus and E. coli and a self-sanitizing residual against S. aureus in the absence of a rinse following treatment. When two fresh water rinses were employed subsequent to treatment, the fabric treated with 2-n-decyl-3-isothiazolone also retained its "self-sanitizing" residual against S. aureus.

TABLE XI

Evaluation of 2-n-decyl-3-isothiazolone

A. Wash Water Sanitization Study (1) Detergent Alone at 0.25% (No Bactericide)
(Number of bacteria/ml. of wash water)

| Schedule for Removal of Wash Water Samples | S. aureus | E. coli | % kill[1] | E. coli S. aureus | % kill[1] |
|---|---|---|---|---|---|
| wash water before inoc. | 0/ml | 0/ml | | 0/ml | |
| 1 minute after inoc. | 70 | 110,000 | | 82,000 | |
| 3 minute after inoc. | 120 | 119,000 | | 88,000 | |
| 5 minute after inoc. | 100 | 131,000 | | 97,000 | |
| 7 minute after inoc. | 140 | 108,000 | | 116,000 | |
| 10 minute after inoc. | 100 | 100,000 | | 92,000 | |
| End of wash cycle (14 min.) | 160 | 99,000 | 0 | 96,000 | 0 |
| Start of Rinse cycle | 0 | 450 | | 860 | |
| End of Rinse cycle | 40 | 5800 | | 6100 | |

(2) Detergent at 0.25% Plus 2-n-decyl-3-isothiazolone at 50 ppm
(Number of bacteria/ml. of wash water)

| Schedule for Removal of Wash Water Samples | S. aureus | E. coli | % kill[1] | E. coli S. aureus | % kill[1] |
|---|---|---|---|---|---|
| wash water before inoc. | 0 | 0 | | 0 | |
| 1 minute after inoc. | 170 | 96,000 | | 70,000 | |
| 3 minute after inoc. | 60 | 90,000 | | 87,000 | |
| 5 minute after inoc. | 100 | 80,000 | | 78,000 | |
| 7 minute after inoc. | 120 | 52,000 | | 65,000 | |
| 10 minute after inoc. | 100 | 29,000 | | 28,000 | |
| End of Wash cycle (14 min.) | 90 | 17,200 | 82.1 | 12,900 | 85.1 |
| Start of Rinse cycle | 0 | 70 | | 30 | |
| End of Rinse cycle | 20 | 520 | 91.0 | 500 | 91.8 |

B. Washed Fabric Swatches (Elution)

| | | Number of Surviving Bacteria/3 inch Swatch | |
|---|---|---|---|
| Wash Solution | Inoculum | Inoculum Swatch | Uninoculated Swatch |
| Detergent alone | S. aureus | 2,000 | 0 |
| Detergent alone | E. coli | 52,000 | 5600 |
| Detergent and isothiazolone | S. aureus | 1,500 | 0 |
| Detergent and isothiazolone | E. coli | 19,500 | 0 |

C. Washed Fabric Swatches (Plated)

| | | Approximate Number of Organisms/Plate | |
|---|---|---|---|
| Wash Solution | Inoculum | Inoculum Swatch | Uninoculated Swatch |
| Detergent alone | E. coli | >10,000 | 110 |
| Detergent and isothiazolone | E. coli | 262 | 4 |

[1]% kill represents the kill over and above that exhibited by detergent alone

TABLE XII

Evaluation of 2-n-octyl-3-isothiazolone (A) Wash Water Sanitization Study (1) Detergent Alone at 0.25% (No Bactericide)
(No. of bacteria/ml. of wash water)

| Schedule for Removal of Wash Water Samples | S. aureus | E. coli | % kill[1] |
|---|---|---|---|
| wash water before inoc. | 0 | 0/ml. | |

TABLE XII-continued

| Evaluation of 2-n-octyl-3-isothiazolone | | | |
|---|---|---|---|
| 1 minute after inoc. | 220 | 90,000 | |
| 3 minute after inoc. | 450 | 92,000 | |
| 5 minute after inoc. | 480 | 96,000 | |
| 7 minute after inoc. | 530 | 73,000 | |
| 10 minute after inoc. | 690 | 86,000 | |
| End of Wash Cycle (14 min.) | 1140 | 91,000 | 0 |
| Start of Rinse Cycle | 0 | 120 | |
| End of Rinse Cycle | 190 | 4630 | |

(2) Detergent at 0.25% Plus 2-n-octyl-3-isothiazolone
(No. of bacteria 1 ml. of wash water)

| Schedule for Removal of Wash Water Samples | S. aureus | E. coli | % kill[1] |
|---|---|---|---|
| wash water before inoc. | 40 | 0 | |
| 1 minute after inoc. | 240 | 92,000 | |
| 3 minute after inoc. | 380 | 85,000 | |
| 5 minute after inoc. | 540 | 96,000 | |
| 7 minute after inoc. | 510 | 69,000 | |
| 10 minute after inoc. | 850 | 46,000 | |
| End of Wash Cycle (14 min.) | 700 | 13,000 | 85.9 |
| Start of Rinse Cycle | 2 | 10 | |
| End of Rinse Cycle | 200 | 290 | 93.7 |

(B) Washed Fabric Swatches (Elution)

| | | Number of Surviving Bacteria/3 inch swatch | |
|---|---|---|---|
| Wash Solution | Inoculum | Inoculum Swatch | Uninoculated Swatch |
| Detergent Alone | E. coli | 106,000 | 2300 |
| Detergent & isothiazolone | E. coli | 16,000 | 0 |

(C) Washed Fabric Swatches (Plated)

| | | Approximate Number of Organism/Plate | |
|---|---|---|---|
| Wash Solution | Inoculum | Inoculum Swatch | Uninoculated Swatch |
| Detergent Alone | E. coli | >10,000 | 81 |
| Detergent & isothiazolone | E. coli | 400 | 3 |

[1] % kill represents the kill over and above that exhibited by detergent alone

TABLE XIII

| | | | | Antibacterial Residuals | | | |
|---|---|---|---|---|---|---|---|
| | | | | Modified AATCC Method | | | |
| | | | | | | 100-1965 t No. of Surviving S. aureus Cells per Fabric Sample | |
| | Conc. of Active Bactericide in treatment Soln. | Theor. Conc. of Act. Bactericide on Fabric | Rinses Following treatment | 90-1965 t Diameter of Zone of Inhibition in mm | | | |
| Isothiazolone | | | | S. aureus | E. coli | Zero time count | After 22 hrs. Exposure |
| None | — | — | None | no zone | no zone | 150,00 | >100,000,000 |
| 2-n-hexyl-3-isothiazolone | 50 ppm. | 500 ppm. | None | 1.5–2.5 | 1.0–1.5 | | 0 |
| 2-n-octyl-3-isothiazolone | 50 ppm. | 500 ppm. | None | 1.0–4.0 | trace | | 5,500 |
| 2-n-decyl-3-isothiazolone | 50 ppm. | 500 ppm. | None | 10 | 1.0–4.0 | | 0 |

Several other isothiazolones were tested by the AATCC Methods 90-1965 T and 100-1965 T, referred to above, and found to give a bacteriostatic or a self-sanitizing residual on fabric against S. aureus and/or E. coli 1000 ppm or less. Among these isothiazolones were 2-n-butyl-3-isothiazolone, 2-n-dodecyl-3-isothiazolone, and 5-chloro-2-methyl 3-isothiazolone.

The above tests and data demonstrate the usefulness of the isothiazolones as laundry sanitizing agents.

EXAMPLE F

Use as Bacteriostats and Mildewstats for Paper and Paper Products

Biocides are incorporated into paper and paper products for the purpose of imparting an antimicrobial residual to control growth of fungi (mildew) and bacteria. The isothiazolones of the invention have been found to be useful as bacteriostats and mildewstats for paper and paper products. When used as paper bacteriostas and mildewstats, the isothiazolones are generally applied to the paper in aqueous solution by a conventional technique such as dipping or spraying. The 3-isothiazolone can have a wide concentration in the solution and will generally be about 0.1 to about 10,000 parts per million by weight, and preferably about 10 to about 1000 parts per million. Depending on the amount of solution uptake by the paper, the concentration of isothiazolone in the treated paper will usually range from about 0.2 to about 30,000 parts per million, and preferably about 25 to 3,000 parts per million by weight.

Isothiazolones were screened for this activity as follows:

Pieces of Whatman No. 1 filter paper were dipped momentarily in solutions containing either 1,000 ppm, 100 ppm, or 10 ppm isothiazolones. The treated papers were air dried, cut into 1½ inch squares, and tested for resistance to bacterial and mildew organisms according to Military Medical Specifications No. 7-864-790.

The results, shown in Table XIV, show that isothiazolone treatments impart bacterial and fungal protection to the paper.

TABLE XIV
Isothiazolones as Paper Bacteriostats and Mildewstats

| Compound Tested | PPM active in Treatment Solution | Bacteriostatic Results Zone of Inhibition vs. *S. aureus*, mm | | Mildewstatic Results Growth of *Chaetomium globosum*[a] | |
|---|---|---|---|---|---|
| | | Rep. 1 | Rep. 2 | Rep. 1 | Rep. 2 |
| 2-n-butyl-4-isothiazolin-3-one | 1000 | 0–5 | 0–5 | 0 | 0 |
| | 100 | 0 | 0 | 0 | 0 |
| | 10 | 0 | 0 | 3+ | 3+ |
| 2-n-hexyl-4-isothiazolin-3-one | 1000 | 13 | 12 | 0 | 0 |
| | 100 | trace | trace | 0 | 0 |
| | 10 | 0 | 0 | 0 | 0 |
| 2-n-octyl-4-isothiazolin-3-one | 1000 | 12 | 12 | 0 | 0 |
| | 100 | trace | 0 | 0 | 0 |
| | 10 | 0 | 0 | 0 | 0 |
| 2-t-octyl-4-isothiazolin-3-one | 1000 | 1–2 | 1–2 | 0 | 0 |
| | 100 | 0 | 0 | 0 | 0 |
| | 10 | 0 | 0 | 3+ | 3+ |
| 2-benzyl-4-isothiazolin-3-one | 1000 | 8–9 | 6–9 | 0 | 0 |
| | 100 | 0 | 0 | 3+ | 2+ |
| | 10 | 0 | 0 | 4+ | 4+ |
| Control (No. Cmpd.) | 0 | 0 | 0 | 4+ | 4+ |

[a] 0 = No Growth (complete inhibition)
1+ = trace of growth
2+ = slight growth
3+ = moderate growth
4+ = heavy growth (no inhibition)

EXAMPLE G

Mildewstats for Leather

Mildewcides are used to prevent mildew damage of stored leather, especially during processing. Isothiazolones of the invention have been found to be useful as mildewstats for leather. When used as leather mildewstats, the isothiazolones are generally applied to the wet-tanned stock in aqueous solution by a conventional technique such as dipping or spraying. The concentration of the isothiazolone in the treatment solution can be varied over a wide concentration range, and will generally be about 0.1 to about 10,000, and preferably about 1 to about 1000, parts per million by weight. The solution can be applied to the leather at any convenient rate, but will commonly be applied at 100% float, that is, at a rate of 100 grams of treatment solution per 100 grams of wet-tanned stock.

Isothiazolone-treated chrome-tanned leather samples were evaluated for residual fungistatic activity by means of the American Chemist Association's Mold Resistance test (L-1). The results, presented in Table XV, show that isothiazolones are effective in this application.

TABLE XV
Mildew Resistance of Chrome-Tanned Leather Treated with Isothiazolones

| Compound Tested | PPM Cmpd.[a] | Treatment Rep. No. | ALCA-L-1 Test Results Mildew Growth After | | | |
|---|---|---|---|---|---|---|
| | | | 1 wk. | 2 wks. | 3 wks. | 4 wks. |
| 2-n-octyl-4-isothiazolin-3-one | 10 | 1 | 0 | 0 | 1+ | 2+ |
| | | 2 | 0 | 0 | 1+ | 2+ |
| | 25 | 1 | 0 | 0 | 0 | 0 |
| | | 2 | 0 | 0 | 0 | 0 |
| | 50 | 1 | 0 | 0 | 0 | 0 |
| | 100 | 1 | 0 | 0 | 0 | 0 |
| | | 2 | 0 | 0 | 0 | 0 |
| 2-n-hexyl-4- | 10 | 1 | 0 | 0 | 1+ | 2+ |
| | | 2 | 0 | 0 | 2+ | 3+ |
| | 25 | 1 | 0 | 0 | 0 | 0 |
| | | 2 | 0 | 0 | 0 | 0 |
| | 50 | 1 | 0 | 0 | 0 | 0 |
| | | 2 | 0 | 0 | 0 | 0 |
| | 100 | 1 | 0 | 0 | 0 | 0 |
| | | 2 | 0 | 0 | 0 | 0 |

[a] Treatment concentration based on wet weight of chrome stock; 100% float.

EXAMPLE H

Application of Mildewcides for Wood Surfaces, Hard Surfaces, and Fabric

Mildewcides are used to control growth of mildew, and subsequent development of mildew odor, discoloration and/or deterioration of wood surfaces, ceramic (hard) surfaces, and fabric in humid environments. Isothiazolones of the invention have been found to be useful in these mildewcidal applications. When used for the surface treatment of wood, ceramic, brick, and fabric, the isothiazolones are generally applied to the material to be treated in aqueous or organic solvent solution by conventional methods in a sufficient amount to saturate the surface, and the treated material can then be dried. The concentration of the isothiazolone in the treatment solution can be varied over a wide concentration range, and will generally be about 0.1 to about 10,000, and preferably about 1 to about 1000, parts per million by weight.

Isothiazolones were found to be effective in tests recommended by the U.S. Environmental Protection Agency for efficacy evaluations of products intended for mildew control on fabric, hard surfaces (ceramic tiles) and wood surfaces.

The tests were performed as follows:

(1) Fabric Test:

The test fungi used in this procedure were *Aspergillus niger* (A. niger ATTC 6275) and *Penicillium glaucum*, both cultures were maintained on Emmon's agar. Spores were harvested after 8–10 days incubation and suspended in 0.85% sodium chloride and 0.2% Triton X-100 surfactant. Test spore suspensions containing 5 million spores/ml of each fungus were mixed 50:50 and sprayed on the test fabric strips (8–20 ounce cotton duck, 1"×3") after chemical treatment.

Chemical treatment of test strips (10 replicates/treatment) was accomplished by immersing fabric for three minutes in test solution. After drying overnight at 37° C., each strip was sprayed with spore inoculum and hung in an 8 ox. screw-capped jar containing 1 inch of sterile water. Observations for fungus growth were made for 4 weeks.

(2) Hard Surface Test (Ceramic Tiles)

An A. niger spore suspension (5 million/ml.) diluted 20:1 with Czapek-Dox nutrient solution was used to inoculate ceramic tiles treated as indicated for fabrics. The dried inoculated tiles were placed on the surface of sterile agar in a petri dish and incubated at 25° C. for 7 days.

(3) Wood Block Test

The test fungus was A. niger and the inoculum prepared as in the above section. Ponderosa pine sapwood blocks (2.5×1.5 cm with hole drilled in one corner) were immersed in treatment solution for 3 minutes, air dried for several hours, and then spray inoculated, hung in jars over water as with the fabric, and incubated at 22°–30° C. for 4 weeks.

The results of these tests, which are summarized in Tables XVI, XVII, and XVIII, show that the isothiazolones are effective as mildewcides in these applications.

TABLE XVI

Mildew Protection of Fabric Strips

| Test Compound | Effective Level[1] (PPM) | | | |
|---|---|---|---|---|
| | 1 wks. | 2 wks. | 3 wks. | 4 wks.[2] |
| 2-n-octyl-4-isothiazolin-3-one | 5 | 5 | 5 | 5 |
| 5-chloro-2-methyl-4-isothiazoline-3-one | 5 | 5 | 5 | 5 |
| Sodium pentachlorophenate | 250 | 250 | 250 | 250 |

[1] Min. effective level to protect 10 replicates.
[2] Incubation period after treatment.

TABLE XVII

Mildew Protection of Hard Surfaces (Ceramic Tiles)

| Test Compound | Minimum effective level to protect 10 replicates after 7 days Incubation, PPM |
|---|---|
| 2-n-octyl-4-isothiazolin-3-one | 5–10 |
| 5-chloro-2-methyl-4-isothiazolin-3-one | >100 |
| Sodium pentachlorophenate | 10,000 |

TABLE XVIII

Mildew Protection of Wood Surfaces

| Test Compound | Minimum Effective Level (PPM) to protect 10 replicate Wood Blocks | | | |
|---|---|---|---|---|
| | 1 wk. | 2 wks. | 3 wks. | 4 wks. |
| 2-n-octyl-4-isothiazolin-3-one | 100 (or less) | 100 | 200 | 200 |
| 5-chloro-2-methyl-4-isothiazolin-3-one (HCl salt)[1] | 10 | 100 | 100–1000 | 100–1000 |
| Sodium pentachlorophenate | 100 | 1000 | 1000 | 1000 |

[1] 2 Replicates in test.

EXAMPLE I

Wood Preservative Application

The isothiazolones of the invention have also been found to be effective in controlling microbial attack on wood. For use as wood preservatives, the isothiazolones can be applied to the wood in aqueous or organic solvent solution by any convenient conventional technique. Generally, the isothiazolone will be applied to give a retention of about 0.001 to about 10, and preferably about 0.005 to about 5, pounds of isothiazolone per cubic foot of wood.

To determine the value of isothiazolones as wood preservatives, the ASTM Laboratory Soil-Block Culture Test (D-1413-61) was performed. The results in Table XIX show wood preservative activity of 2-n-octyl-3-isothiazolone in terms of decreased percentage weight loss of isothiazolone treated wood compared to control without test compound in toluene treatment solution

TABLE XIX

Isothiazolones as Wood Preservatives

| PPM- 2-n-octyl-4-isothiazolin-3-one in toluene | Retention pounds isothiazolone per cubic foot of wood | Percentage Wt. loss of Block | |
|---|---|---|---|
| | | vs. *Lentinus lepideus* culture | vs. *Lenzites trabea* culture |
| 0 | 0 | 44.6 | 62.7 |
| 8 | 0.002 | 35.3 | 38.1 |
| 17 | 0.005 | 25.5 | 56.4 |
| 33 | 0.009 | 26.1 | 54.9 |
| 67 | 0.019 | 21.4 | 32.8 |
| 134 | 0.038 | 8.4 | 17.2 |
| 267 | 0.076 | 2.8 | 1.7 |

EXAMPLE J

Fungicidal Disinfectant

In the process of chemical disinfection, a fungicidal agent can be used to kill the fungus contaminants associated with disease. To demonstrate efficacy in this application, isothiazolones were evaluated in the A.O.A.C. Fungicidal Test.

The results presented in Table XX, which shows the maximum effective dilution vs. *Trichophyton interdigitale*-ATCC 9533, the causative agent for athlete's foot, demonstrate further fungicidal effectiveness of isothiazolones of the invention.

TABLE XX

Evaluation of Isothiazolones Against *Trichophyton interdigitals*

| Compound | Maximum Effective Dilution (PPM) |
|---|---|
| 2-n-butyl-4-isothiazolin-3-one | 1:800 (1250 PPM) |
| 2-n-hexyl-4-isothiazolin-3-one | 1:1500 (600 PPM) |
| 2-n-octyl-4-isothiazolin-3-one | 1:1000 (1000 PPM) |
| 2-t-octyl-4-isothiazolin-3-one | 1:800 (1250 PPM) |
| 2-n-nonyl-4-isothiazolin-3-one | >1:1200 (<830 PPM) |
| 2-n-dodecyl-4-isothiazolin-3-one | >1:1200 (<830 PPM) |
| 2-cyclohexyl-4-isothiazolin-3-one | >1:1200 (<830 PPM) |
| 2-methyl-4,5-dichloro-4-isothiazolin-3-one | 1:800 (1250 PPM) |

EXAMPLE K

Cosmetic Preservative

Microbicides are used as preservatives to prevent the growth of microorganisms in cosmetic formulations and to kill microbial contaminants introduced during manufacturing and during use of the product. Isothiazolones of the invention have been found to be efficacious in this application. When used in cosmetic formulations, the concentration of isothiazolone can be varied greatly depending on the particular formulation, and will generally be about 1 to about 20,000, and preferably about 10 to about 3,000, parts per million by weight.

To evaluate the effectiveness of isothiazolones of the invention as cosmetics preservatives, the following standard cosmetic formulations were prepared:

Formulation No. 1 cetyl alcohol, 20% mineral oil, 20%
sorbitan monooleate, 0.5%
polyoxyethylene sorbitol monooleate, 4.5%
deionized water, 55%

Formulation No. 2 mineral oil 24.5%
sorbitan monostearate, 1.5%
polyoxyethylene soritan monostearate, 8.5%
deionized water, 65.5%

Samples (50 g) containing varying concentrations of isothiazolones were inoculated with a pooled suspension of the following microorganisms:

*Pseudomonas oleoverans*
*Escherichia coli*
*Staphylococcus aureus*
Serrotia sp.
Aspergillus sp.
Penicillium sp.
Streptomyces sp.
*Saccharomyces cerevisiae*
*Cladospoorium resinae* and incubated at room temperature. The samples were re-inoculated monthly for 8 months to simulate contamination during use of the product (Table XXII) or were inoculated only initially, to simulate contamination during manufacturing (Table XXI). Effectiveness was based on the absence of viable microorganisms, as determined by various microbiological techniques.

The results of these tests, shown in Tables XXI and XXII, show the effectiveness of isothiazolones of the invention in preventing the growth of microorganisms in cosmetic preservatives.

TABLE XXI

Isothiazolones as Cosmetic Preservatives in Formulations Contaminated During Preparation

| Compound | Minimum Effective Concentration (ppm) Formulation No. | |
|---|---|---|
| | 1 | 2 |
| 2-cyclohexyl-4-isothiazolin-3-one | 1000(2)[1] | 1000(2) |
| 2-n-butyl-4-isothiazolin-3-one | 100(8) | 1000(8) |
| 2-n-cyclopropyl-4-isothiazolin-3-one | 500(8) | 500(8) |
| 2-methyl-4-isothiazolin-3-one (HCl) | 250(8) | 500(8) |
| 2-n-butyl-5-chloro-4-isothiazolin-3-one | 100(8) | 50(8) |
| 2-n-propyl-5-chloro-4-isothiazolin-3-one | 50(8) | 50(8)[2] |
| 2-ethyl-5-chloro-4-isothiazolin-3-one | 50(8) | 50(8)[2] |
| 2-methyl-5-chloro-4-isothiazolin-3-one (HCl) | 50(8) | 50(8) |
| 2-methyl-4-bromo-5-chloro-4-isothiazolin-3-one | 50(8) | 500(8) |
| 2-phenyl-5-chloro-4-isothiazolin-3-one | 250(8) | 1000(6) |
| formaldehyde | >1000(1) | 1000(6) |
| methyl p-hydroxybenzoate | >3000(1) | >3000(1) |
| propyl p-hydroxybenzoate | >3000(1) | >3000(1) |

[1](Months) from inoculation
[2]failure vs. fungi at 1000 ppm

TABLE XXII

Isothiazolones as Cosmetic Preservatives in Formulations Re-contaminated Monthly

| Compound | Minimum Effective Concentration (ppm) Formulation No. | |
|---|---|---|
| | 1 | 2 |
| 2-n-butyl-4-isothiazolin-3-one | 250 (8)[1] | 250 (8) |
| 2-n-cyclopropyl-4-isothiazolin-3-one | 500 (8) | 500 (8) |
| 2-methyl-4-isothiazolin-3-one (HCl) | 500 (8) | 500 (8) |
| 2-n-butyl-5-chloro-4-isothiazolin-3-one | 100 (8) | 50 (8) |
| 2-n-propyl-5-chloro-4-isothiazolin-3-one | 50 (8) | 50 (8) |
| 2-ethyl-5-chloro-4-isothiazolin-3-one | 50 (8) | 50 (8) |
| 2-methyl-5-chloro-4-isothiazolin-3-one (HCl) | 50 (8) | 50 (8) |
| 2-methyl-4-bromo-5-chloro-4-isothiazolin-3-one | 50 (8) | >1000 (8) |
| 2-phenyl-5-chloro-4-isothiazolin-3-one | 500 (8) | >1000 (<8) |
| Methyl p-hydroxybenzoate | >3000 (<8) | >3000 (<8) |

[1](Months) from initial inoculation

EXAMPLE L

Soap Bacteriostat Application

Bacteriostats and bactericides are employed in soap, as a means to control bacterial microflora on the skin. The isothiazolones of the invention have been found to be effective as bacteristatic and bactericidal additives to soap. While the concentration of the isothiazolone in the soap can be varied greatly depending on the soap formulation, the isothiazolone used, the degree of activity desired, and related factors, it will generally be present at about 0.01 to about 3%, and preferably about 0.1 to about 3% by weight.

Isothiazolones were evaluated for this application using a serial dilution test and the published Protein Adsorption Test of Bechtold and Lawrence (Proceeding of the Scientific Section of the Toilet Goods Association, 24, December, 1955).

The test used in these evaluations was a serial dilution test similar to that described above for Table III, except dilutions were made also in the presence of soap. Biological compatibility of isothiazolones with soap was indicated in this test when the maximum bacteriostatic dilution of the isothiazolone was not adversely affected by the presence of soap. The results are shown in Table XXIII.

The Protein Adsorption Test of Bachtold and Lawrence shows the potential of soap bacteriostat candidates in terms of adsorption. As shown in Table XXIV, adsorption was indicated by the presence of a zone of inhibition.

TABLE XXIII

Serial-Dilution Test for Soap Bacteriostats

| Compound | Maximum Bacteriostatic[1] Dilution | |
|---|---|---|
| | Without Soap | With Soap[2] |
| 2-n-octyl-4-isothiazolin-3-one | 1:128,000 | 1:128,000 |
| 2-n-decyl-4-isothiazolin-3-one | 1:1,000,000 | 1:1,000,000 |
| 2-n-dodecyl-4-isothiazolin-3-one | 1:1,000,000 | 1:1,000,000 |
| 2-methyl-5-chloro-4-isothiazolin-3-one | 1:128,000 | 1:128,000 |
| 2,2'-dihydroxy-3,5,6-3',5',6'-hexachlorodiphenyl methane (Hexachlorophene) | 1:2,000,000 | 1:2,000,000 |

[1]vs. *Staph. Aureus* (ATCC 6538)
[2]Ivory Flakes, 50:1 ratio soap to compound

TABLE XXIV

Protein Adsorption
Soap Bacteriostat Test

| Compound | Average Zone of Inhibition, mm[1] |
| --- | --- |
| 2-n-octyl-4-isothiazolin-3-one | trace |
| 2-n-dodecyl-isothiazolin-3-one | trace |
| 2-isopropyl-5-chloro-4-isothiazolin-3-one | 15.5 |
| 2-n-butyl-4-bromo-4-isothiazolin-3-one | 1.0 |
| 2-n-hexyl-4-bromo-5-chloro-4-isothiazolin-3-one | 8.5 |
| 2-n-hexyl-4-bromo-4-isothiazolin-3-one | 2.0 |
| 2-n-octyl-5-chloro-4-isothiazolin-3-one | 7.0 |
| 2-(4-chlorophenyl-)-5-chloro-4-isothiazolin-3-one | 1.3 |
| 2-cyclohexyl-4,5-dichloro-4-isothiazolin-3-one | 7.0 |
| hexachlorophene | 8.0 |
| No compound | 0 |

[1]Zone diameter minus diameter of protein film disc

The above data demonstrate the effectiveness of isothiazolones of the invention as soap bacteriostats.

The isothiazolones were also found to be quite useful as microbicides in fiber spin finish formulation, such as nylon spin finish formulations. In evaluating the isothiazolones in this application, samples of naturally contaminated spin finish formulations were obtained and used to inoculate uncontaminated formulations to which an isothiazolone had been added. After a one month incubation, the test formulations were examined for contamination, and then recontaminated. In one such test, 2-benzyl-3-isothiazolone was found to be very effective in controlling microbial contamination in fiber spin finish formulations at a concentration of 250 parts per million or less.

It is to be understood that changes and variations may be made without departing from the spirit and scope of the invention as defined by the appended claims.

We claim:

1. A cutting oil composition comprising a major proportion of a cutting oil and a biocidal amount of a compound of the formula

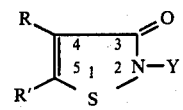

wherein

Y is an unsubstituted or substituted alkyl, alkenyl, or alkynyl group of 1 to 18 carbon atoms, an unsubstituted or substituted cycloalkyl group having a 3 to 6 carbon atom ring and up to 12 carbon atoms, an unsubstituted or substituted aralkyl group of up to 10 carbon atoms, or an unsubstituted or substituted aryl group of up to 10 carbon atoms, R is hydrogen, halogen, or a ($C_1$-$C_4$) alkyl group, and R' is hydrogen, halogen, or a ($C_1$-$C_4$) alkyl group, or a salt of a compound of the above formula with a strong acid.

2. The cutting oil composition of claim 1 which comprises, in addition, an effective amount of an emulsifying agent.

3. The composition of claim 2 wherein Y is (1) an unsubstituted alkyl group of 1 to to 18 carbon atoms, (2) a substituted alkyl group having at least one hydrogen atom replaced by hydroxy, halo, cyano, alkylamino, dialkylamino, phenylamino, halophenylamino, carboxy, carbalkoxy, alkoxy, aryloxy, or carbamoxy, wherein the total number of carbon atoms in the substituted alkyl group does not exceed 18, (3) an unsubstituted or halo-substituted alkenyl group of 2 to 18 carbon atoms, (4) unsubstituted or halo-substituted alkynyl group of 2 to 28 carbon atoms, (5) an unsubstituted or alkyl-substituted cycloalkyl group having a 3 to 6 carbon atom ring and up to 12 carbon atoms, (6) an unsubstituted or a halo-, lower alkyl-, or lower alkoxy-substituted aralkyl group wherein the total number of carbon atoms in the aralkyl group does not exceed 10, or (7) an unsubstituted or halo-, nitro-, lower alkyl-, or lower carbalkoxy-, substituted aryl group wherein the total number of carbon atoms in the aryl group does not exceed 10; R is hydrogen, halogen, or a ($C_1$-$C_4$)alkyl group, and R' is hydrogen, halogen, or a ($C_1$-$C_4$)alkyl group, or a salt of a compound of the above formula with a strong acid.

4. The composition of claim 3 in which R is hydrogen or halogen, and R' is hydrogen or halogen.

5. The composition of claim 4 in which Y is an unsubstituted alkyl or cycloalkyl group, R' is chlorine, and R is hydrogen.

6. The composition of claim 5 in which Y is an alkyl group.

* * * * *